(12) United States Patent
Su et al.

(10) Patent No.: US 11,793,453 B2
(45) Date of Patent: Oct. 24, 2023

(54) DETECTING AND MEASURING SNORING

(71) Applicant: Fitbit, Inc., San Francisco, CA (US)

(72) Inventors: Hao-Wei Su, Cambridge, MA (US);
Logan Niehaus, Alameda, CA (US);
Conor Joseph Heneghan, Campbell, CA (US); Jonathan David Charlesworth, San Francisco, CA (US);
Subramaniam Venkatraman, Lafayette, CA (US); Shelten Gee Jao Yuen, Berkeley, CA (US)

(73) Assignee: Fitbit, Inc., San Francisco, CA (US)

( * ) Notice: Subject to any disclaimer, the term of this patent is extended or adjusted under 35 U.S.C. 154(b) by 33 days.

(21) Appl. No.: 16/890,931

(22) Filed: Jun. 2, 2020

(65) Prior Publication Data
US 2020/0383633 A1    Dec. 10, 2020

Related U.S. Application Data

(63) Continuation-in-part of application No. 16/431,576, filed on Jun. 4, 2019, now Pat. No. 11,229,369.

(51) Int. Cl.
*A61B 5/00* (2006.01)
*A61B 5/08* (2006.01)
(Continued)

(52) U.S. Cl.
CPC ........ *A61B 5/4809* (2013.01); *A61B 5/02416* (2013.01); *A61B 5/0816* (2013.01);
(Continued)

(58) Field of Classification Search
CPC . A61B 5/4809; A61B 5/02416; A61B 5/1102; A61B 5/681; A61B 5/742;
(Continued)

(56) References Cited

U.S. PATENT DOCUMENTS 8,287,460 B2   10/2012  Broadley et al.
10,136,853 B2  11/2018  Heinrich et al.
(Continued)

FOREIGN PATENT DOCUMENTS

CN   108670200   10/2018
EP     2653107   10/2013
(Continued)

OTHER PUBLICATIONS

International Application No. PCT/US2020/035968, Search Report and Written Opinion dated Sep. 16, 2020, 8 pages.
(Continued)

*Primary Examiner* — Gary Jackson
*Assistant Examiner* — Sebastian X Lukjan
(74) *Attorney, Agent, or Firm* — Dority & Manning, P.A.

(57) ABSTRACT

Approaches described herein can capture an audio signal using at least one microphone while a user of an electronic device is determined to be asleep. At least one audio frame can be determined from the audio signal. The at least one audio frame represents a spectrum of frequencies detected by the at least one microphone over some period of time. One or more sounds associated with the at least one audio frame can be determined. Sleep-related information can be generated. The information identifies the one or more sounds as potential sources of sleep disruption.

12 Claims, 24 Drawing Sheets

(51) Int. Cl.
*G10L 25/51* (2013.01)
*A61B 5/024* (2006.01)
*A61B 5/11* (2006.01)

(52) U.S. Cl.
CPC ............ *A61B 5/1102* (2013.01); *A61B 5/681* (2013.01); *A61B 5/742* (2013.01); *G10L 25/51* (2013.01)

(58) Field of Classification Search
CPC .......... A61B 5/0816; A61B 2562/0204; A61B 5/4815; G10L 25/51; G10L 25/63; G10L 15/26
See application file for complete search history.

(56) References Cited

U.S. PATENT DOCUMENTS

| | | | | |
|---|---|---|---|---|
| 10,791,986 B1* | 10/2020 | Kahn | ................... | A61B 5/0002 |
| 10,945,659 B1* | 3/2021 | Kahn | ................... | A61B 5/4812 |
| 2006/0266356 A1* | 11/2006 | Sotos | ................... | A61B 5/4806 |
| | | | | 128/204.23 |
| 2010/0175726 A1* | 7/2010 | Eli | ................... | A61M 16/0666 |
| | | | | 134/166 C |
| 2012/0240941 A1 | 9/2012 | Rosenman et al. | | |
| 2013/0144190 A1 | 6/2013 | Bruce et al. | | |
| 2013/0324788 A1* | 12/2013 | Holley | ............... | A61M 16/0633 |
| | | | | 600/28 |
| 2015/0039110 A1 | 2/2015 | Abeyratne et al. | | |
| 2015/0150501 A1 | 6/2015 | George et al. | | |
| 2015/0173671 A1 | 6/2015 | Paalasmaa et al. | | |
| 2015/0348538 A1* | 12/2015 | Donaldson | .............. | G10L 17/22 |
| | | | | 704/235 |
| 2017/0049391 A1 | 2/2017 | Melker | | |
| 2017/0128003 A1* | 5/2017 | Lim | ...................... | A61B 5/6898 |
| 2017/0172494 A1 | 6/2017 | Warren et al. | | |
| 2017/0325779 A1 | 11/2017 | Spina et al. | | |
| 2018/0106897 A1 | 4/2018 | Shouldice et al. | | |
| 2018/0214051 A1* | 8/2018 | Larson | ................... | H04W 4/38 |
| 2018/0256069 A1 | 9/2018 | McMahon | | |
| 2018/0303413 A1* | 10/2018 | Hassan | ................. | A61B 5/4803 |
| 2019/0000350 A1* | 1/2019 | Narayan | ................... | A61B 5/08 |
| 2019/0029563 A1* | 1/2019 | Sels | ..................... | A61B 5/0002 |
| 2019/0038179 A1 | 2/2019 | Tanriover et al. | | |
| 2019/0038216 A1 | 2/2019 | Ser et al. | | |
| 2019/0201267 A1* | 7/2019 | Demirli | ................... | A61B 5/4809 |
| 2019/0298224 A1 | 10/2019 | Rahman et al. | | |

FOREIGN PATENT DOCUMENTS

| | | |
|---|---|---|
| JP | 6154372 B2 | 6/2017 |
| WO | 2017083754 A1 | 5/2017 |
| WO | 2017178205 A1 | 10/2017 |
| WO | WO-2017178205 A1 * 10/2017 | ........... A61B 5/0004 |

OTHER PUBLICATIONS

Extended European Search Report for Application No. 20819591.7, dated Oct. 10, 2022, 11 pages.

* cited by examiner

664 — Typical sound level

The overall sound level in your bedroom consists of snoring and background noise combined.

31 dBA
Typical noise level in your bedroom dBA is the abbreviation of A-weighted decibel, which is an expression of the relative loudness of sounds in air as perceived by the human ear.

Here are a few of the most common sounds measured in dBA:

- A soft whisper is around 30 dBA
- Rainfall is around 50 dBA
- A coffee grinder is around 70 to 80 dBA
- A blender is around 90 dBA

FIGURE 6G

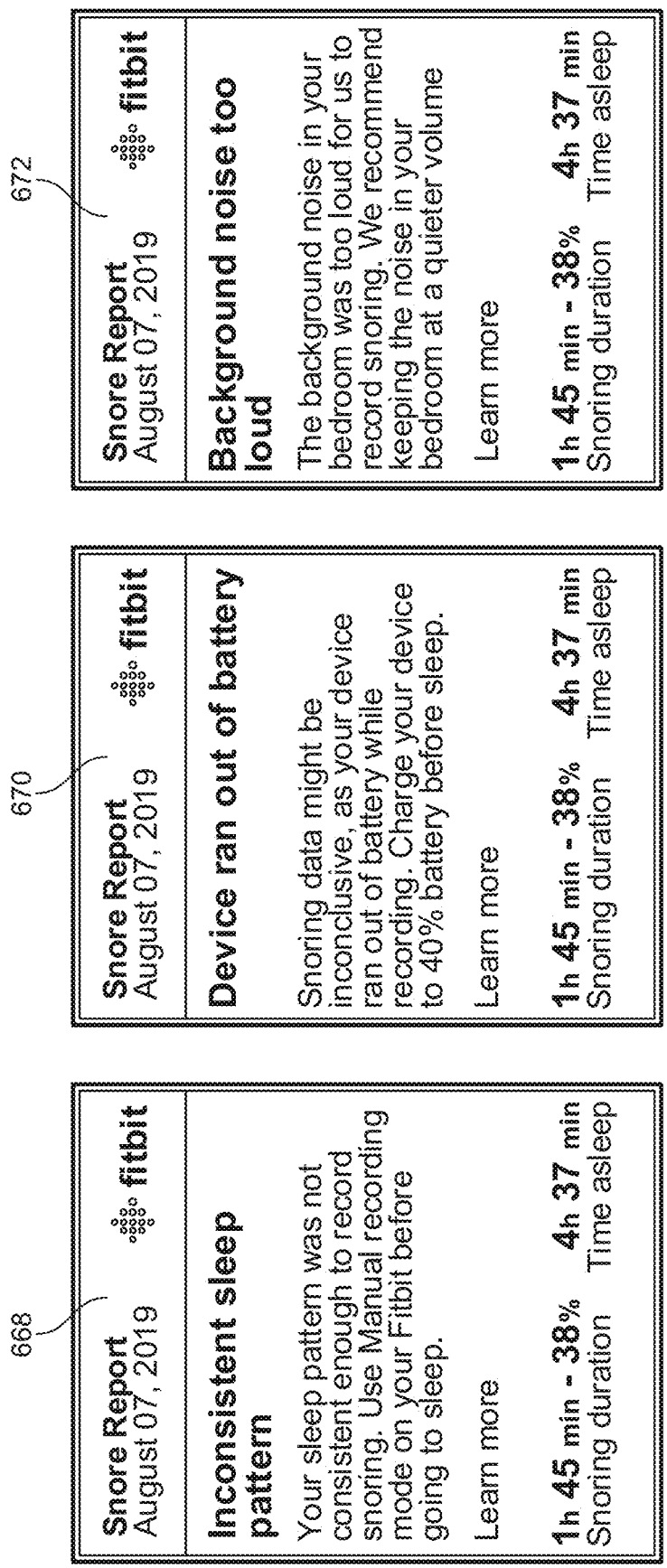

800

```
┌─────────────────────────────────────────────┐
│ Determine one or more breathing phase       │
│ patterns over a period of time using audio  │
│ data captured by at least one microphone,   │
│ the audio data including one or more snores │
│                     802                     │
└─────────────────────────────────────────────┘
                      ↓
┌─────────────────────────────────────────────┐
│ Determine a breathing phase pattern         │
│ included within the period of time, based   │
│ at least in part on sensor data captured by │
│ one or more sensors in an electronic device │
│                     804                     │
└─────────────────────────────────────────────┘
                      ↓
┌─────────────────────────────────────────────┐
│ Determine that a first breathing phase      │
│ pattern represented by the audio data, and  │
│ a second breathing phase pattern            │
│ represented by the sensor data are          │
│ correlated                                  │
│                     806                     │
└─────────────────────────────────────────────┘
                      ↓
┌─────────────────────────────────────────────┐
│ Determine that the first breathing phase    │
│ pattern represented by the audio data and   │
│ the second breathing phase pattern          │
│ represented by the sensor data both         │
│ correspond to a user wearing the electronic │
│ device                                      │
│                     808                     │
└─────────────────────────────────────────────┘
```

```
┌─────────────────────────────────────────────────────┐
│ Capture an audio signal using at least one          │
│ microphone while a user of an electronic device is  │
│ determined to be asleep                             │
│ 852                                                 │
└─────────────────────────────────────────────────────┘
                         │
                         ▼
┌─────────────────────────────────────────────────────┐
│ Determine at least one audio frame from the audio   │
│ signal, wherein the at least one audio frame        │
│ represents a spectrum of frequencies detected by    │
│ the at least one microphone over some period of time│
│ 854                                                 │
└─────────────────────────────────────────────────────┘
                         │
                         ▼
┌─────────────────────────────────────────────────────┐
│ Determine one or more sounds associated with        │
│ the at least one audio frame                        │
│ 856                                                 │
└─────────────────────────────────────────────────────┘
                         │
                         ▼
┌─────────────────────────────────────────────────────┐
│ Generate sleep-related information, wherein the     │
│ information identifies the one or more sounds as    │
│ potential sources of sleep disruption               │
│ 858                                                 │
└─────────────────────────────────────────────────────┘
```

FIGURE 8B

DETECTING AND MEASURING SNORING

CROSS-REFERENCE TO RELATED APPLICATIONS

This application is a continuation-in-part of U.S. patent application Ser. No. 16/431,576, filed on Jun. 4, 2019 and entitled "DETECTING AND MEASURING SNORING", which is incorporated herein by reference in its entirety.

TECHNICAL FIELD

The present technology relates to the field of wearable devices. More particularly, the present technology relates to techniques for collecting and processing biometric data.

BACKGROUND

Wearable electronic devices have gained popularity among consumers. A wearable electronic device may track a user's activities using a variety of sensors. Data captured from these sensors can be analyzed in order to provide a user with information that can help the user to maintain a healthy lifestyle. In order to determine information about a user's activities, a conventional wearable electronic device collects activity data and runs computations on that data, such as on-device, remotely (e.g., in a server environment), or a combination of the two.

SUMMARY

Various embodiments of the present technology can include systems, methods, and non-transitory computer readable media configured to capture an audio signal using at least one microphone while a user of the electronic device is determined to be asleep. At least one audio frame can be determined from the audio signal, wherein the at least one audio frame represents a spectrum of frequencies detected by the at least one microphone over some period of time. One or more sounds associated with the at least one audio frame can be determined. Sleep-related information can be generated, wherein the information identifies the one or more sounds as potential sources of sleep disruption.

In some embodiments, determining the one or more sounds associated with the at least one audio frame further comprises determining information describing the one or more sounds based at least in part on a machine learning model that relates the spectrum of frequencies represented by the at least one audio frame to the one or more sounds.

In some embodiments, the systems, methods, and non-transitory computer readable media can further be configured to extracting a set of features based on the spectrum of frequencies represented by the at least one audio frame; providing the set of features to the machine learning model; and obtaining information describing the one or more sounds from the machine learning model.

In some embodiments, the set of features comprise at least mel-frequency cepstral coefficients (MFCCs) that describe the spectrum of frequencies represented by the at least one audio frame.

In some embodiments, determining the one or more sounds associated with the at least one audio frame further comprises determining one or more sources of the one or more sounds and identifying the one or more sources of the one or more sounds in the generated sleep-related information.

In some embodiments, the one or more sounds associated with the at least one audio frame are determined as the audio signal is being captured.

In some embodiments, the systems, methods, and non-transitory computer readable media can further be configured to discard the at least one audio frame after the one or more sounds associated with the at least one audio frame are determined.

In some embodiments, the at least one microphone used to capture the audio signal is included in one or both of the electronic device or a computing device separate from the electronic device.

In some embodiments, the systems, methods, and non-transitory computer readable media can further be configured to provide the generated sleep-related information through an interface accessible through the electronic device or a computing device separate from the electronic device.

In some embodiments, the interface provides one or more options for audibly replaying the at least one audio frame associated with the one or more sounds.

In some embodiments, the sleep-related information provides one or more of: a total amount of time the user was determined to be sleeping, one or more periods of time during which the user was determined to be awake, or one or more periods of time during which the user was determined to be snoring.

In some embodiments, the sleep-related information provides one or more of: a total amount of time during which the user was snoring, a percentage of time during which the user was snoring relative to the total amount of time the user was determined to be sleeping, or a percentage range of time during which the user was snoring relative to the total amount of time the user was determined to be sleeping.

In some embodiments, the sleep-related information provides a categorization of the one or more periods of time during which the user was determined to be snoring based on snoring intensity.

In some embodiments, the categorization labels the one or more periods of time during which the user was determined to be snoring as a first level of snoring, a second level of snoring, or a third level of snoring.

In some embodiments, the sleep-related information identifies a correlation between one or more periods of time during which the user was determined to be awake and the one or more sounds identified as potential sources of sleep disruption.

In some embodiments, the sleep-related information provides a listing of sounds detected while the user was asleep.

In some embodiments, the listing identifies a detected sound and a respective number of instances of the detected sound while the user was asleep.

In some embodiments, the sleep-related information provides one or more of: a baseline noise level while the user was asleep, an average noise level while the user was asleep, a highest noise level while the user was asleep, or a total count of sounds detected while the user was asleep.

It should be appreciated that many other features, applications, embodiments, and/or variations of the disclosed technology will be apparent from the accompanying drawings and from the following detailed description. Additional and/or alternative implementations of the structures, systems, non-transitory computer readable media, and methods described herein can be employed without departing from the principles of the disclosed technology.

BRIEF DESCRIPTION OF THE DRAWINGS

FIGS. 6A-6K illustrate example diagrams of user interfaces, according to an embodiment of the present technology.

FIGS. 7, 8A-8B, and 9-11 illustrate example methods, according to embodiments of the present technology.

Figure 1A:
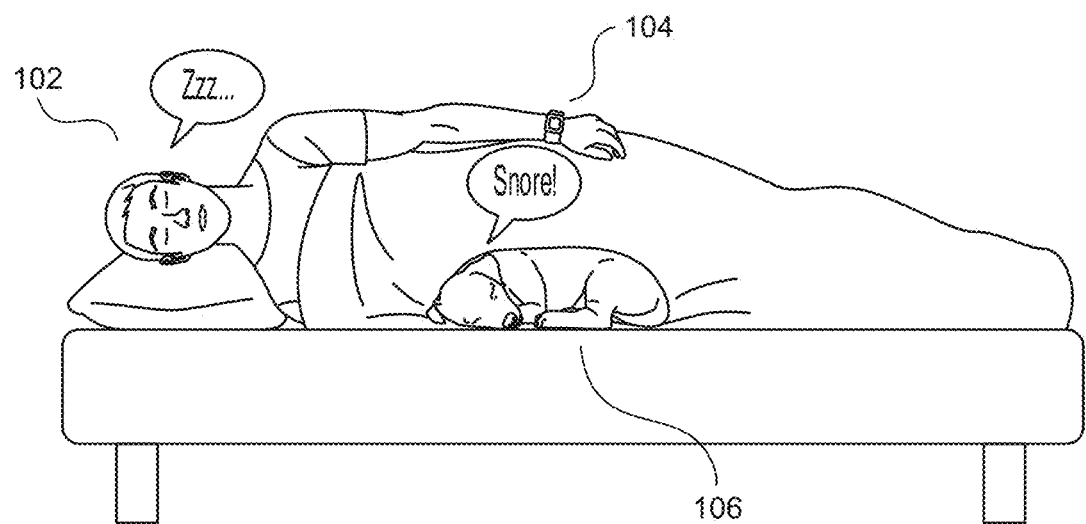
FIGS. 1A-1C illustrate example diagrams, according to an embodiment of the present technology.

The figures depict various embodiments of the disclosed technology for purposes of illustration only, wherein the figures use like reference numerals to identify like elements. One skilled in the art will readily recognize from the following discussion that alternative embodiments of the structures and methods illustrated in the figures can be employed without departing from the principles of the disclosed technology described herein.

DETAILED DESCRIPTION

Conventional approaches for determining whether a user of a wearable device is snoring may rely on audio data captured by a microphone. For example, the audio data may reflect spectral properties indicative of a person snoring. These conventional approaches are prone to error, however, when multiple entities (e.g., persons, animals) are present in a room. In such instances, while audio data captured by a microphone in the room can still reflect spectral properties indicative of an entity snoring, the audio data alone generally cannot be used to isolate a source of the snoring. Further, even when only one entity is present in a room, conventional approaches typically cannot determine various sleep-related information, such as an intensity of snoring produced by the entity. The importance of sleep to physical and mental well-being cannot be refuted. In fact, numerous scientific studies have shown that lack of sleep can affect one's overall health and make one prone to serious medical conditions, such as obesity, heart disease, high blood pressure, and diabetes. Thus, a need exists for innovative computer technology solutions that can solve technical problems associated with a need to identify users of wearable devices that snore and can also determine sleep-related information that helps those users improve their sleep habits and, ultimately, their overall well-being, among other things.

An improved approach rooted in computer technology overcomes the foregoing and other disadvantages associated with conventional approaches specifically arising in the realm of computer technology. In various embodiments, sensor data captured by sensors of a wearable device can be used in combination with audio data to determine whether a user of the wearable device is snoring. In general, a "snore" can refer to sound caused by or otherwise associated with breathing disturbances while a person sleeps. The snore may be audible to a human (such as a traditional snore) and/or detected by electronic sensors, such as a microphone in a wearable device or other device proximate to the sleeping person. If a determination is made that the user of the wearable device is snoring, various information (e.g., snore metrics) describing the snoring can be determined for the user. For example, the information may identify one or more durations of snoring activity detected for the user over some period of time. In some instances, a determination that the user is not snoring can also be informative. For example, a user 102 of a wearable device 104 may be sleeping in a room with a pet animal 106, as illustrated in the example of FIG. 1A. In this example, the animal 106 is snoring while the user 102 is not. In various embodiments, a determination can be made whether the snoring originates from the user 102 of the wearable device 104 or another entity present in the room based on factors such as a combination of audio data containing the snoring (e.g., audio data captured by a microphone in the wearable device 104) and sensor data captured by the wearable device 104. For example, a first breathing phase pattern can be determined based on audio data recording the animal 106 snoring over some period of time. Further, a second breathing phase pattern can be determined based on sensor data captured by one or more sensors in the wearable device 104 over the same period of time. For example, the second breathing phase pattern can be determined based on sensor data captured by one or more photoplethysmogram (PPG) sensors, motion detectors (e.g., accelerometers), respiration monitors (e.g., sensors capable of detecting an expansion and contraction of the chest or abdomen, sensors capable of detecting inhalations and/or exhalations, etc.), electrodermal activity (EDA) sensors, temperature sensors, or a combination thereof. Such sensor data can provide physiological information describing the user 102 of the wearable device 104, such as when the user 102 is inhaling and exhaling. In such embodiments, an amount of correlation can be determined between the first breathing phase pattern determined based on audio data and the second breathing phase pattern determined based on sensor data. Based on the amount of correlation, a determination can be made whether the snoring originates from the user 102 of the wearable device 104 or another entity present in the room (e.g., the animal 106). In the example of FIG. 1A, a determination is made that the snoring does not originate from the user 102 of the wearable device 104 based on a correlation between the first breathing phase pattern and the second breathing phase pattern failing to match or meet a threshold qualitative and/or quantitative value (e.g., signal phase matching, a derived "score" or other derived quantity, etc.). Such determinations can be especially useful so that the user 102 can be provided with accurate sleep-related information and recommendations without false positives.

Figure 1B:
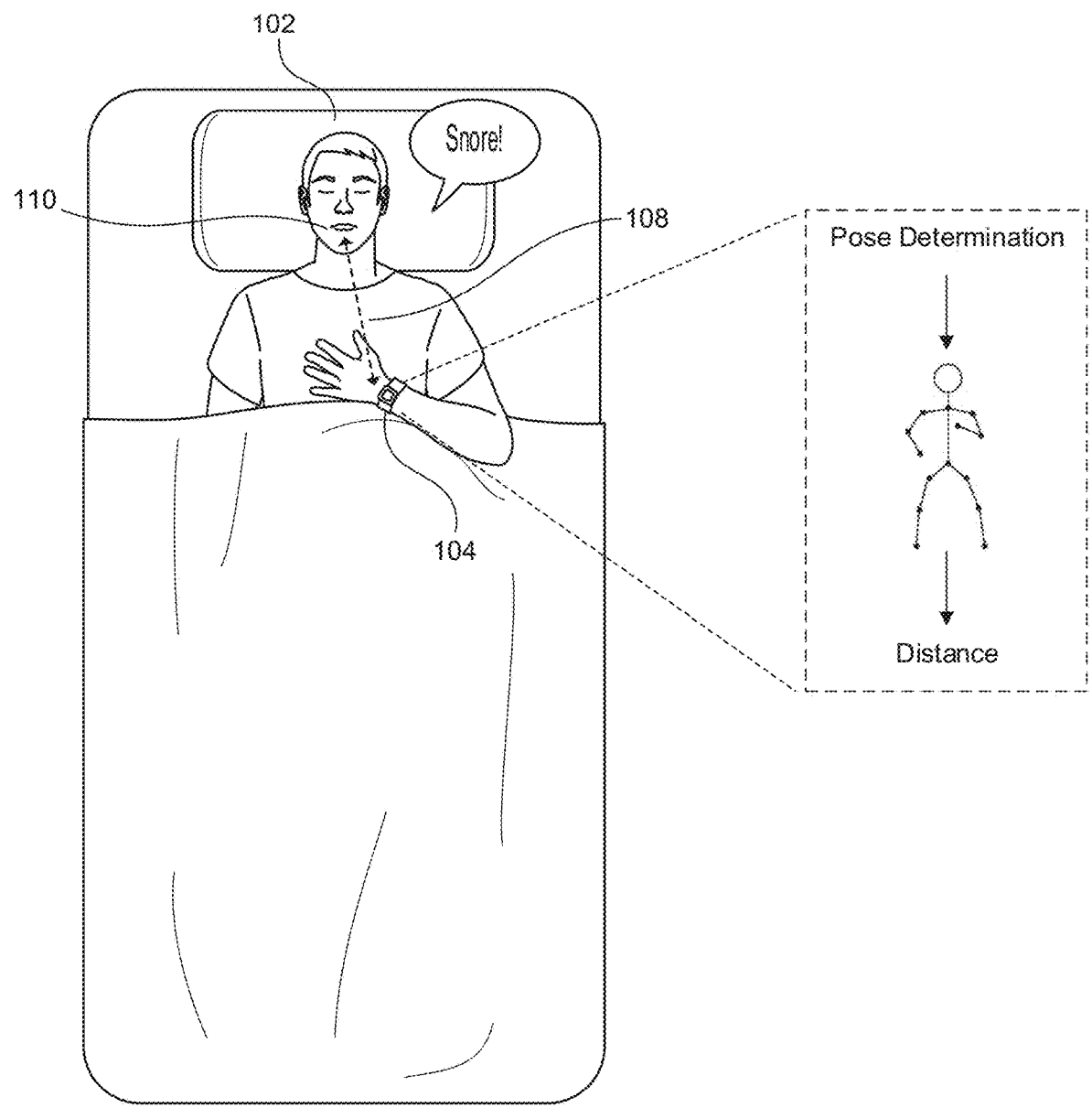

If a determination is made that the user 102 of the wearable device 104 is snoring, various information (e.g., snore metrics) describing the snoring can be determined for the user 102. In some instances, the accuracy of such information, such as snore intensity, can be affected based on factors such as a distance 108 between the wearable device 104 that is recording the user's snoring and the mouth 110 of the user 102 from which the snoring originates, as illustrated in the example of FIG. 1B. For example, a snore that was determined to be very intense (e.g., 75 dB) due to the wearable device 104 being positioned near to the user's mouth 110 may actually be moderate in intensity (e.g., 50 dB) when distance is factored. Thus, in various embodiments, the distance 108 can be determined (or estimated) to improve the accuracy of various snore metrics for the user. For example, the distance 108 can be determined based on a wrist pose and sleep pose of the user 102. In some embodiments, the poses may be determined based on a relationship between an orientation of the wearable device 104, an attitude of the wearable device 104 to magnetic north, and musculoskeletal constraints imposed by a rigid human pose model. In some embodiments, the poses may be determined based on sensor data such as a ballistocardiogram (BCG) pattern detected by the wearable device 104, positional information associated with the wearable device 104, such as that provided by an altimeter, gyroscope, or other sensor, etc. In some embodiments, the distance 108 can be adjusted (or estimated) based on a height of the user 102 of the wearable device. Many variations are possible, including combinations of the various embodiments described above.

Figure 1C:
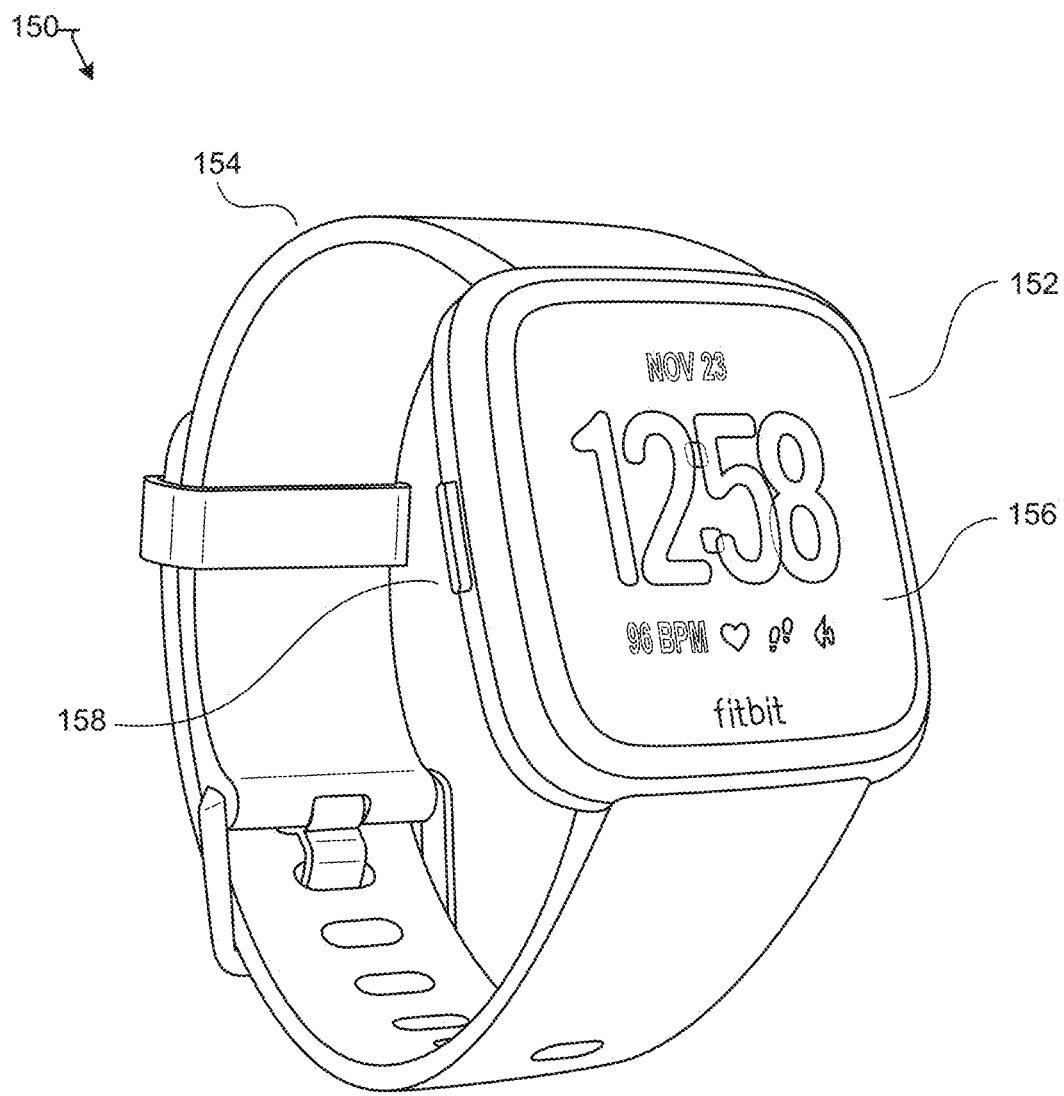

FIG. 1C illustrates an example of a wearable device 150. The wearable device 150 includes both a computing device 152 as well as a band portion 154. The wearable device 150 can include a display screen 156 for viewing and accessing various information (e.g., snore metrics). The display screen 156 may be a capacitive touchscreen, which may be configured to respond to contact with electrical charge-holding members or tools, such as a human finger. The wearable device 150 may include one or more buttons 158, which may be selected to provide various user input. The wearable device 150 may incorporate one or more functional components (or modules) designed for determining one or more physiological metrics associated with a user (or wearer) of the wearable device 150, such as a heart rate sensor, body temperature sensor, and an environmental temperature sensor, to name some examples. Such modules may be disposed or associated with an underside/backside of the wearable device 150, and may be in contact (or substantially in contact) with human skin when the wearable device 150 is worn. In some embodiments, sensors may be disposed on an interior (or skin-side) of the wearable device 150. More details describing the wearable device 150 are provided below in reference to FIGS. 2A-2C.

Figure 2A:
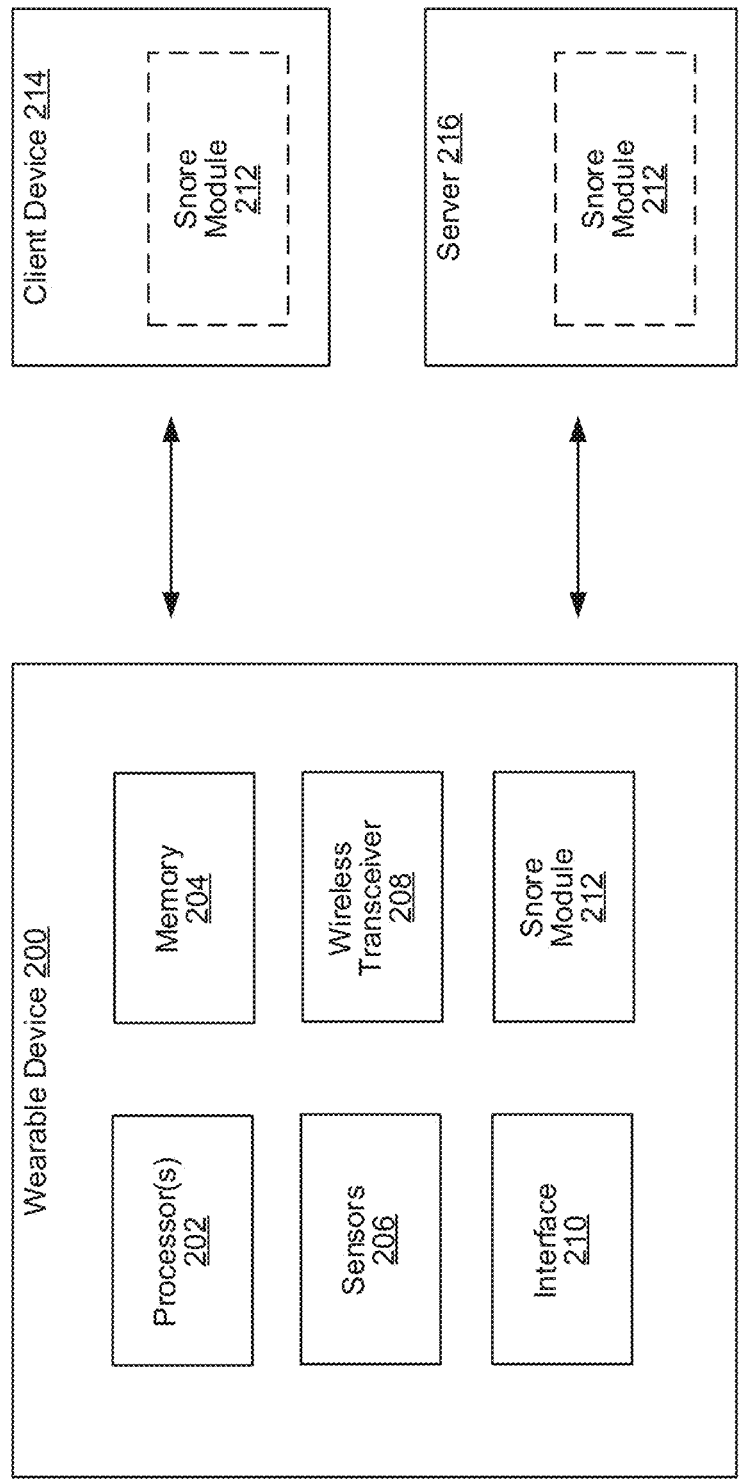
FIG. 2A is a block diagram illustrating an example environment including a wearable device, according to an embodiment of the present technology.

FIG. 2A is a block diagram illustrating an example wearable device 200, according to an embodiment of the present technology. The wearable device 200 may be a smartwatch, a watch, a wrist-wearable fitness-, health-, or activity-monitoring device, and the like, although the concepts described herein may be implemented in any type of portable or wearable devices including one or more sensors. For example, the wearable device 200 may be implemented as the wearable device 150 of FIG. 1C. The wearable device 200 may include one or more processors 202, memory 204, sensors 206, a wireless transceiver 208, an interface 210, and a snore module 212. The processors 202 can interact with the memory 204, sensors 206, wireless transceiver 208, interface 210, and snore module 212 to perform various operations as described herein. The memory 204 may store instructions for causing the processors 202 to perform certain operations (or actions). In some embodiments, the sensors 206 may collect various types of sensor data that can be used by the wearable device 200 to detect and respond to various scenarios. The wearable device 200 can be configured to wirelessly communicate with one or more client devices 214 and/or servers 216, for example, through the wireless transceiver 208 either directly or when in range of a wireless access point (e.g., via a personal area network (PAN) such as Bluetooth pairing, wireless local area network (WLAN), wide area network (WAN), etc.). The client device 214 may be a smartphone, a tablet, or another mobile device executing software (e.g., a mobile application) configured to perform one or more operations described herein.

The server 216 may be implemented using one or more computing systems executing software configured to perform one or more operations described herein. Depending on the implementation, the operations described herein may be performed solely by the wearable device 200 or by the wearable device 200, the client device 214, and the server 216 in a distributed manner. For example, in some embodiments, the snore module 212 (or some operations performed by the snore module 212) can be implemented by the client device 214 and/or the server 216. The wearable device 200 may collect one or more types of data from the sensors 206 and/or from external devices. The collected data can be communicated to other devices (e.g., the client device 214 and/or the server 216), thus permitting the collected data to be processed by the client device 214 and/or the server 216 using any and all of the approaches described herein. The collected data can also be viewed, for example, using a web browser or software application. For example, while being worn by a user, the wearable device 200 may perform biometric monitoring by calculating and storing the user's step count based on sensor data collected by the sensors 206. The wearable device 200 may transmit data representative of the user's step count to a user account for a web service (e.g., fitbit.com), computer, mobile phone, and/or health station where the data may be stored, processed, and/or visualized by the user. The wearable device 200 may measure or calculate other metric(s) in addition to, or in place of, the user's step count. Such metric(s) may include, but are not limited to, energy expenditure, e.g., calorie burn; floors climbed and/or descended; heart rate; heartbeat waveform; heart rate variability; heart rate recovery; respiration; oxygen saturation (402); blood volume; blood glucose; skin moisture and skin pigmentation level; location and/or heading (e.g., via a GPS, global navigation satellite system (GLONASS), or a similar system); elevation; ambulatory speed and/or distance traveled; blood pressure; blood glucose; skin conduction; skin and/or body temperature; muscle state measured via electromyography; brain activity as measured by electroencephalography; weight; body fat; caloric intake; nutritional intake from food; medication intake; sleep periods (e.g., clock time, sleep phases, sleep quality and/or duration); pH levels; hydration levels; and respiration rate, to name some examples. The wearable device 200 may also measure or calculate metrics related to an environment of the user, such as, for example, barometric pressure, weather conditions (e.g., temperature, humidity, pollen count, air quality, rain/snow conditions, wind speed), light exposure (e.g., ambient light, ultra-violet (UV) light exposure, time and/or duration spent in darkness), noise exposure, radiation exposure, and/or magnetic field. Furthermore, the wearable device 200 may obtain data from the sensors 206, and may calculate metrics derived from such data (or, in some embodiments, transmit, in a synchronous or asynchronous manner, some or all such sensor data (or a subset thereof) to another computing device (such as a server environment or a personal computing device, for calculation of one or more said metrics, which may then be transmitted back to the wearable device and/or used to generate commands which, when transmitted to the wearable device, cause the wearable device to perform one or more actions (e.g., displaying a message, generating an alert, etc.). For example, the wearable device 200 may calculate the user's stress or relaxation levels based on a combination of heart rate variability, skin conduction, noise pollution, and/or sleep quality. In another example, the wearable device 200 may determine the efficacy of a medical intervention, for example, medication, based on a combination of data relating to medication intake, sleep, and/or activity. In yet another example, the wearable device 200 may determine the efficacy of an allergy medication based on a combination of data relating to pollen levels, medication intake, sleep and/or activity. These examples are provided for illustration only and are not intended to be limiting or exhaustive. More details describing the sensors 206 are provided below in reference to FIG. 2B. More details describing the snore module 212 are provided below in reference to FIG. 2C.

Figure 2B:
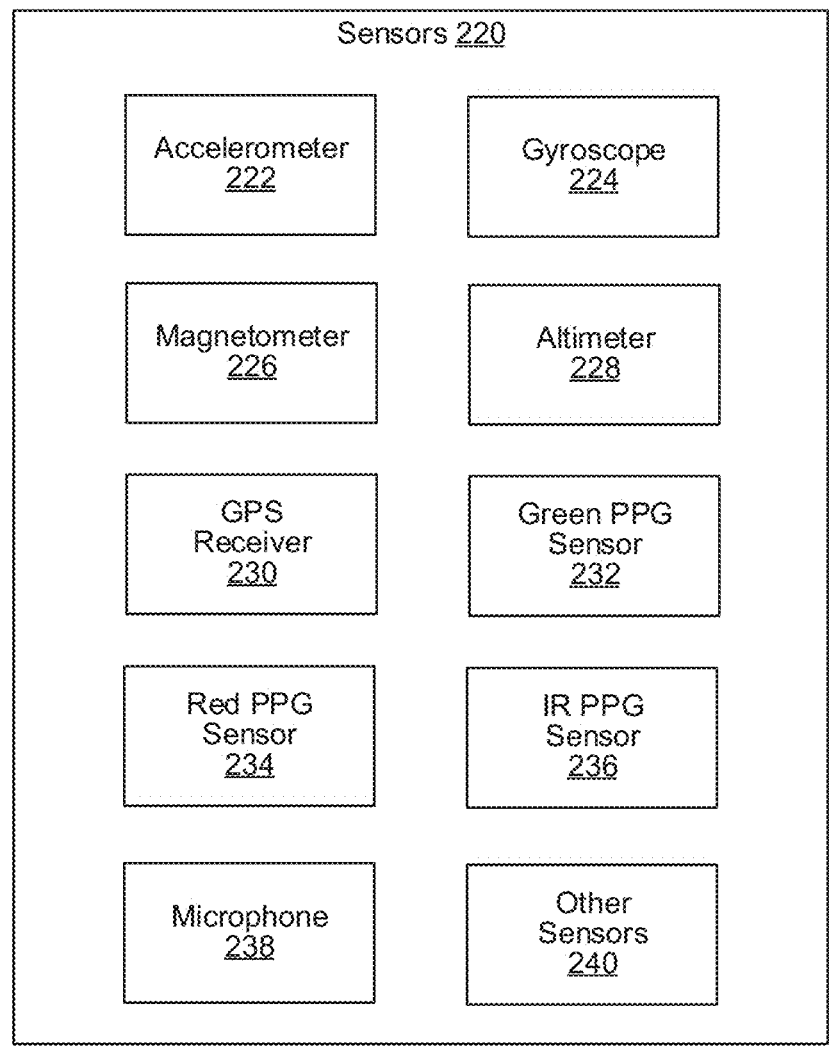
FIG. 2B is a block diagram illustrating example sensors which may be in communication with a processor of the wearable device, according to an embodiment of the present technology.

FIG. 2B is a block diagram illustrating a number of example sensors 220 that may be included in the wearable device 200, according to an embodiment of the present technology. For example, the wearable device 200 can include at least one accelerometer 222 (e.g., a multi-axis accelerometer), a gyroscope 224, a magnetometer 226, an altimeter 228, a GPS receiver 230, a green photoplethysmogram (PPG) sensor 232, a red PPG sensor 234, an infrared (IR) PPG sensor 236, one or more microphones 238, and one or more other sensors 240, all of which may be in communication with the processors 202. The one or more other sensors 240 can include, for example, a temperature sensor, an ambient light sensor, a galvanic skin response (GSR) sensor, a capacitive sensor, a humidity sensor, a force sensor, a gravity sensor, a piezoelectric film sensor, and a rotation vector sensor, all of which may be in communication with the processors 202. The processors 202 may use input received from any sensor or combination of sensors to detect the start of an activity (or exercise) and/or to track metrics for the activity. In some embodiments, some of the sensors 220 may be placed on the chest of a user, a mattress on which the user sleeps, or a bedside table of the user while the wearable device 200 is worn by the user. Although the example of FIG. 2B illustrates a variety of sensors, in other embodiments the wearable device 200 may include a fewer number of sensors and/or any other subsets and combinations of the sensors. Additionally, in some embodiments, the GPS receiver 230 may be implemented by the client device 214 rather than the wearable device 200. In these implementations, the wearable device 200 may wirelessly communicate with the client device 214 to access geolocation data. In related aspects, the processors 202 and other component(s) of the wearable device 200 may be implemented using any of a variety of suitable circuitry, such as one or more microprocessors, application specific integrated circuits (ASICs), field programmable gate arrays (FPGAs), discrete logic, software, hardware, firmware or any combinations thereof. When the techniques are implemented partially in software, a device may store instructions for the software in a suitable, non-transitory computer-readable medium and execute the instructions in hardware using one or more processors to perform the techniques of this disclosure. In further related aspects, the processors 202 and other component(s) of the wearable device 200 may be implemented as a System-on-Chip (SoC) that may include one or more central processing unit (CPU) cores that use one or more reduced instruction set computing (RISC) instruction sets, a GPS receiver 230, a wireless wide area network (WWAN) radio circuit, a WLAN radio circuit, and/or other software and hardware to support the wearable device 200. Again, many variations are possible.

Figure 2C:
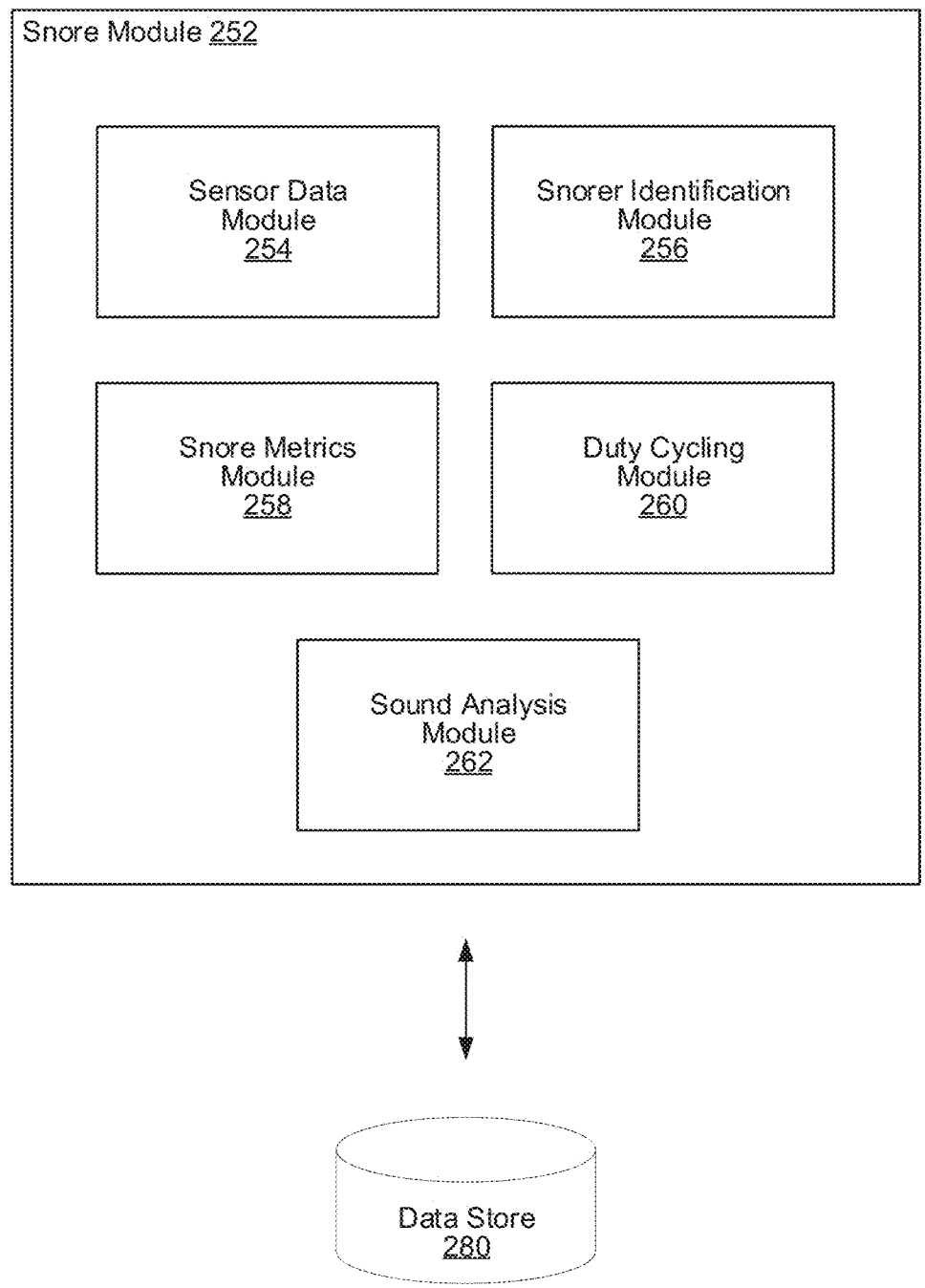
FIG. 2C is a block diagram illustrating an example snore module, according to an embodiment of the present technology.

FIG. 2C illustrates an example snore module 252, according to an embodiment of the present disclosure. As shown in the example of FIG. 2C, the snore module 252 can include a sensor data module 254, a snorer identification module 256, a snore metrics module 258, and a duty cycling module 260. In some instances, the snore module 252 can interact with at least one data store 280 to access sensor data collected by a wearable device in which the snore module 252 is implemented, such as the wearable device 200 of FIG. 2A. The components (e.g., modules) shown in this figure and all figures herein are provided as examples, and other implementations may include additional, fewer, integrated, or different components. In some embodiments, the snore module 252 can be implemented, in part or in whole, as software, hardware, or any combination thereof. In general, a module, as discussed herein, can be associated with software, hardware, or any combination thereof. In some implementations, one or more functions, tasks, and/or operations of modules can be carried out or performed by software routines, software processes, hardware, and/or any combination thereof. In some cases, the snore module 252, or at least a portion thereof, can be implemented, in part or in whole, as software running on the wearable device. In some embodiments, the snore module 252 can be implemented, in part or in whole, as software running on one or more computing devices. For example, the snore module 252, or at least a portion thereof, can be implemented as or within an application (e.g., app), a program, or an applet, etc., running on a user computing device, such as the client device 214 of FIG. 2A. In some instances, the snore module 252 can, in part or in whole, be implemented within or configured to operate in conjunction with a server, such as the server 216 of FIG. 2A. It should be understood that there can be many variations or other possibilities.

The sensor data module 254 can be configured to access sensor data captured by various sensors of the wearable device 200, as described above in reference to FIGS. 2A-2B. For example, the sensor data may include data captured by one or more microphones, photoplethysmogram (PPG) sensors, accelerometers, gyroscopes, magnetometers, and altimeters, to name some examples. The sensor data module 254 can obtain such sensor data, for example, directly from sensors associated with the wearable device 200 in real-time (or near real-time) or from the data store 280 in which such sensor data can be stored. In some instances, the sensor data module 254 can obtain sensor data captured by one or more external sensors that are separate from the wearable device 200. For example, a standalone microphone that is separate from the wearable device 200 may be used to record (or capture) audio data of a user snoring. Many variations are possible. In some embodiments, sensor data can be captured and/or supplemented by one or more non-wearable devices (e.g., a bedsheet or other non-wearable device). For example, in some embodiments, a non-wearable device can be configured to detect human motion based on ultrasonic waves. Again, many variations are possible.

The snorer identification module 256 can be configured to determine whether a user of the wearable device is snoring. For example, the snorer identification module 256 can determine whether the user is snoring based on audio data captured by one or more microphones associated with the wearable device and sensor data captured by one or more sensors associated with the wearable device. More details describing the snorer identification module 256 are provided below in reference to FIG. 3.

The snore metrics module 258 can be configured to determine snore information (e.g., metrics) for the user of the wearable device. For example, the snore metrics module 258 can determine one or more durations of snoring activity for the user during the period of time. In another example, the snore metrics module 258 can determine changes to a snore level or intensity of the user over the period of time. In some embodiments, such metrics can be determined based on an estimated distance (or proximity) between the wearable device and the mouth of the user. More details describing the snore metrics module 258 are provided below in reference to FIG. 4.

The duty cycling module 260 can be configured to selectively activate at least one microphone in the wearable device based on a breathing (or respiratory) phase pattern determined for the user. For example, the breathing phase pattern may be determined based on any of the techniques described herein. In various embodiments, the duty cycling module 260 can time the activation of the microphone to record snores produced by the user. That is, based on the breathing phase pattern, the duty cycling module 260 can activate the microphone when the user inhales (e.g., when snores are produced) and deactivate the microphone after inhalation (e.g., after a snore is recorded). For example, if the user snores every four seconds, then the duty cycling module 260 can activate the microphone just before a snore is expected to occur while deactivating (or turning off) the microphone between snores. This selective activation helps conserve power and storage space that would otherwise have been expended by the wearable device if the microphone were to remain active during the user's entire sleep cycle (e.g., overnight). In some embodiments, the duty cycling module 260 can determine when the user's sleep activity is disturbed and can activate the microphone to record sounds that may have caused the disturbance. In such embodiments, the duty cycling module 260 can apply generally known classifiers for detecting when the user is or is not in a sleep state. In some embodiments, the user can interact with the wearable device to disable duty cycling so that the microphone can record the user's sleep activity in its entirety, for example, for purposes of conducting a complete sleep diagnosis for the user. Many variations are possible.

The sound analysis module 262 can be configured to identify and categorize sounds based on audio signals captured by one or more microphones associated with the wearable device. For example, the sound analysis module 262 can enable the microphones associated with the wearable device to capture an audio signal (or recording) while a user of the wearable device is determined to be asleep. The audio signal can capture sounds produced by the user while sleeping (e.g., snoring) in addition to ambient noises that occurred in the user's sleep environment. In this example, the sound analysis module 262 can analyze the audio signal to identify sounds (e.g., engine noise, barking, etc.) and respective sources of the sounds (e.g., vehicle, animal, etc.). In various embodiments, the categorized sounds can be used to identify potential sources of sleep disruption which the user may not be aware of. In some embodiments, information describing the categorized sounds can be provided through an interface. For example, in some embodiments, the interface can provide options to replay the categorized sounds, as illustrated in the example of FIG. 6B. In some embodiments, the interface can identify the categorized sounds in a list of sounds that may have disrupted the user's sleep, as illustrated in the example of FIG. 6C. In some embodiments, information describing the categorized sounds can be provided in a snore report, as illustrated in the example of FIG. 6D. The snore report can provide various sleep-related information including a total amount of time the user was determined to be sleeping, any periods of time during which the user was determined to be awake, and any periods of time during which the user was determined to be snoring, for example. In some embodiments, the sleep-related information can identify a correlation between one or more periods of time during which the user was determined to be awake and any categorized sounds that were identified as potential sources of sleep disruption during those periods of time. Many variations are possible.

The sound analysis module 262 can analyze and categorize audio based on various approaches for processing audio signals. In some embodiments, the sound analysis module 262 can analyze and categorize audio based on machine learning. For example, the sound analysis module 262 can obtain an audio signal to be analyzed. The sound analysis module 262 can segment the audio signal into a set of audio frames. Each audio frame can represent a spectrum of frequencies of sound for some period of time. Depending on the implementation, the audio frames may or may not overlap. In such embodiments, the sound analysis module 262 can analyze an audio frame by extracting a set of features from a spectrum of frequencies represented by the audio frame. For example, in some embodiments, the set of features can include mel-frequency cepstral coefficients (MFCCs) that describe the spectrum of frequencies represented by the audio frame. The sound analysis module 262 can provide the set of features to a machine learning model that has been trained to categorize the set of features as a particular sound. Depending on the implementation, the machine learning model may be trained to categorize the set of features based on varying specificity. For example, the set of features may be categorized as a particular sound source (e.g., vehicle, animal, furnace, etc.) or as a distinct sound (e.g., vehicle horn, dog bark, etc.). In some embodiments, the machine learning model can be trained based on sets of features extracted from a set of labeled audio frames. For example, the audio frames can be labeled based on sounds represented in the audio frames. Many variations are possible. For example, in some embodiments, audio frames can be clustered based on their extracted features. Each cluster of audio frames can be labeled, for example, as corresponding to a particular sound. The clusters of audio frames can then be used to train the machine learning model.

In some embodiments, the sound analysis module 262 can analyze and categorize audio based on a privacy-by-design approach. In such embodiments, the sound analysis module 262 can analyze and categorize audio in real-time (or near real-time) as an audio signal is being captured. The sound analysis module 262 can automatically discard audio data as soon as the audio data is categorized using the approaches described herein. Under this approach, the sound analysis module 262 can still provide information describing sounds that were identified in a sleep environment without saving audio data.

Figure 3:
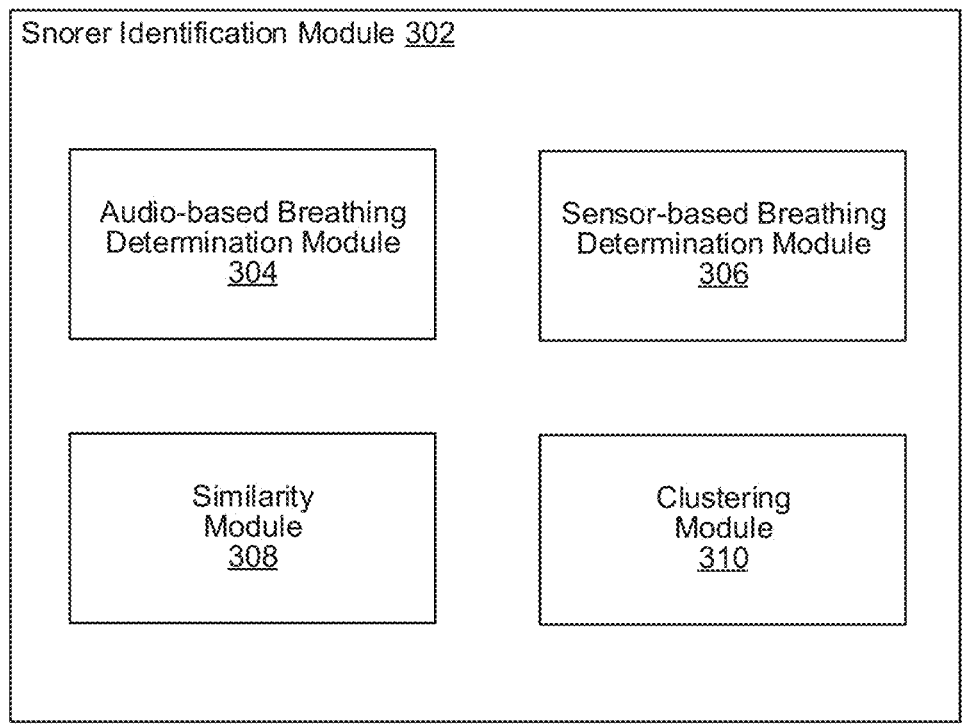
FIG. 3 illustrates an example snorer identification module, according to an embodiment of the present technology.

FIG. 3 illustrates an example of a snorer identification module 302, according to an embodiment of the present disclosure. In some embodiments, the snorer identification module 256 of FIG. 2C can be implemented with the snorer identification module 302. As shown in the example of FIG. 3, the snorer identification module 302 can include an audio-based breathing determination module 304, a sensor-based breathing determination module 306, a similarity module 308, and a clustering module 310.

The audio-based breathing determination module 304 can be configured to determine (or estimate) a breathing phase of an entity (e.g., person, animal) based on audio data of the entity snoring. In general, snoring can refer to distinctive sounds that occur when air flows through relaxed tissues in the entity's throat, thereby causing the relaxed tissues to vibrate as the entity inhales and exhales. For example, in various embodiments, the audio-based breathing determination module 304 can obtain audio data recording the entity snoring over some period of time. The audio data can provide an audio spectrum that includes spectral properties indicative of the entity snoring at various time intervals, as illustrated by the audio data 502 in the example of FIG. 5. The audio spectrum can reflect a corresponding energy level (or sound pressure level) associated with each snore produced by the entity. Depending on the implementation, the audio data can be captured by one or more microphones in the wearable device, by one or more standalone microphones that are separate from the wearable device (e.g., a microphone in a mobile device), or a combination thereof. In some embodiments, the audio data can be pre-processed. For example, in some embodiments, the audio data can be pre-processed by eliminating (or reducing) environmental or ambient noise captured in the audio data using generally known noise reduction techniques. Such pre-processing can help improve snore-related estimations, such as snore level (or volume) estimation. In some embodiments, the audio data can be pre-processed by eliminating (or reducing) movement noise captured in the audio data. For example, the audio data may be captured by a microphone in the wearable device. In this example, the microphone may capture movement noise when the entity moves during sleep. In some instances, this movement noise can distort the entity's snoring activity as captured by the microphone. To improve the detection and processing of the entity's snoring activity, the audio-based breathing determination module 304 can drop portions of audio data that include instances of movement noise. For example, the audio-based breathing determination module 304 can detect movement based on sensor data and can classify blanket noise against sounds made by the entity when breathing (i.e., inhaling and exhaling). In some embodiments, instances of movement noise can be identified by correlating motion detected by one or more accelerometers in the wearable device. In some embodiments, instances of movement noise can be identified by correlating motion detected by one or more PPG sensors in the wearable device. Many variations are possible. In various embodiments, the audio-based breathing determination module 304 can determine (or estimate) a breathing (or respiratory) phase of the entity based on the audio data based on generally known techniques. The breathing phase of the entity based on the audio data can be used to determine whether the entity snoring corresponds to a user of the wearable device based on sensor data captured by the wearable device, as described below.

The sensor-based breathing determination module 306 can be configured to determine (or estimate) a breathing phase of the user of the wearable device based on sensor data captured by the wearable device. For example, in some embodiments, the sensor-based breathing determination module 306 can obtain sensor data from one or more photoplethysmogram (PPG) sensors in the wearable device. For example, the PPG sensors can include a green PPG sensor, a red PPG sensor, an infrared (IR) PPG sensor, or a combination thereof. Each PPG sensor can apply generally known light-based technology to independently measure the rate of blood flow as controlled by the user's heart as it pumps blood, i.e., heart rate signals. These measurements can be indicative of the user snoring at various time intervals, as illustrated by the PPG data 504 in the example of FIG. 5. In various embodiments, measurements taken by each PPG sensor can be used to determine (or estimate) a respective breathing (or respiratory) phase for the user based on generally known techniques. In such embodiments, an amount of correlation can be determined between the breathing phase of the user based on measurements captured by a PPG sensor and the breathing phase of the entity based on the audio data, as determined by the audio-based breathing determination module 304. If a threshold correlation exists, the user of the wearable device can be determined to be the source of the snores captured in the audio data, as described below in reference to the similarity module 308. Other types of sensor data can be used to determine such correlation. For example, in some embodiments, breathing rate and phase information can be determined using lower frequency variations in a DC level of a PPG signal as captured by a PPG sensor. In some embodiments, breathing rate and phase information can be determined from changes in the amplitude of AC variations in a PPG signal that correspond to heart beats. Such variations in the PPG signal can result from underlying physiological changes in the mechanical properties and chemical composition of the blood and arteries in the tissue from which the PPG signal was sensed by the PPG sensor. In some embodiments, the sensor-based breathing determination module 306 can obtain sensor data from one or more accelerometers in the wearable device. In general, an accelerometer can measure the rate of change in the velocity of the wearable device. In some instances, these measurements can be indicative of the user snoring at various time intervals, as illustrated by the accelerometer data 506 in the example of FIG. 5. In various embodiments, measurements taken by an accelerometer can be used to determine (or estimate) a respective breathing phase for the user based on generally known techniques. For example, the user of the wearable device may be resting the wearable device on their chest. In this example, measurements taken by an accelerometer in the wearable device can be used to determine a breathing phase as the user inhales and exhales. In such embodiments, an amount of correlation can be determined between the breathing phase of the user based on measurements captured by the accelerometer and the breathing phase of the entity based on the audio data, as described below. Many variations are possible. For example, in various embodiments, other types of sensor data can be used to determine (or estimate) breathing phase, such as a ballistocardiogram (BCG) pattern detected by the wearable device, an electrocardiogram (ECG) signal determined by the wearable device, or an impedance cardiography (ICG) signal determined by the wearable device. Such signals may be determined based on dry electrodes in the wearable device that inject and sense current, for example.

The similarity module 308 can be configured to determine an amount of similarity (or correlation) between the breathing phase determined based on audio data and the breathing phase determined based on sensor data (e.g., PPG sensors, accelerometers, etc.). In various embodiments, the similarity module 308 can apply generally known techniques for determining an amount of correlation between the breathing phase determined based on audio data and the breathing phase determined based on sensor data. For example, the similarity module 308 can determine the amount of correlation based on autocorrelation or cross-correlation. In some embodiments, the similarity module 308 can determine that a threshold amount of correlation exists between the breathing phase determined based on audio data and the breathing phase determined based on sensor data. If a threshold amount of correlation exists, then a determination can be made that the snoring captured by the audio data originates from the user of the wearable device. In this instance, the audio data can be associated with the user of the wearable device. In some embodiments, once this association is made, the snoring activity can be processed and analyzed to provide various insights to the user of the wearable device, as illustrated in the examples of FIGS. 6A-6J. Many variations are possible. For example, in some embodiments, the similarity module 308 can determine an amount of correlation between breathing phases based on breathing (or respiratory) rate values. For example, a breathing rate value can indicate how frequently a breath is taken (e.g., breath every 3 seconds). In some embodiments, the similarity module 308 can determine a first breathing rate value for the breathing phase determined based on audio data. The first breathing rate value can be determined based on frequency and phase information describing the breathing phase determined based on audio data. Similarly, the similarity module 308 can determine a second breathing rate value for the breathing phase determined based on sensor data. The second breathing rate value can be determined based on frequency and phase information describing the breathing phase determined based on sensor data. In such embodiments, a determination can be made that the snoring captured by the audio data corresponds to the user of the wearable device when the first breathing rate value matches the second breathing rate value. In some embodiments, the similarity module 308 can represent the amount of correlation as a probability that measures a likelihood of the snoring activity captured by the audio data originating from the user of the wearable device. Many variations are possible.

The clustering module 310 can be configured to generate clusters of snoring activity based on audio data. For example, in some instances, the audio data may capture multiple entities snoring over some period of time. In such instances, it can be difficult to distinguish between snoring produced by one entity over snoring produced by another entity. To help distinguish between snoring entities, in various embodiments, the clustering module 310 can generate clusters by extracting various spectral features from the audio data based on generally known techniques, such as Mel-frequency cepstrum (MFC). For example, the extracted spectral features can be binned into different frequency bands. Further, an respective amount of energy for each band can be determined in log scale. The bands can then be clustered based on their respective amounts of energy with respect to time. In various embodiments, bands representing snoring activity by different entities can be included in different corresponding clusters. For example, bands representing snoring activity from a first entity can be included in a first cluster while bands representing snoring activity from a second entity can be included in a second cluster. In various embodiments, such clusters can be used to determine which snoring activity corresponds to a user wearing the wearable device. In the foregoing example, a determination can be made whether some portion of data (e.g., a set of frequency bands over some period of time) included in the first or second cluster has a threshold amount of correlation to a breathing (or respiratory) rate determined (or estimated) based on sensors in the wearable device with respect to time. If a determination is made that a threshold amount of correlation exists between a portion of data from the first cluster and the breathing rate determined by the sensors of the wearable device, then a determination can be made that the snoring activity represented by the first cluster was produced by the user of the wearable device. Alternatively, if a determination is made that a threshold amount of correlation exists between a portion of data from the second cluster and the breathing rate determined by the sensors of the wearable device, then a determination can be made that the snoring activity represented by the second cluster was produced by the user of the wearable device. In various embodiments, once a cluster is determined to be associated with a user, audio data represented by the cluster can be evaluated to determine various sleep- and snore-related information for the user as described herein.

Figure 4:
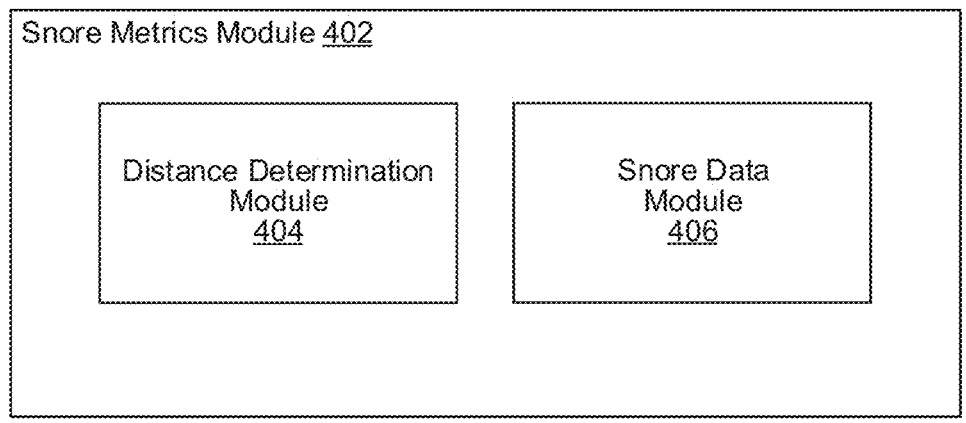
FIG. 4 illustrates an example snore metrics module, according to an embodiment of the present technology.

FIG. 4 illustrates an example of a snore metrics module 402, according to an embodiment of the present disclosure. In some embodiments, the snore metrics module 258 of FIG. 2C can be implemented with the snore metrics module 402. As shown in the example of FIG. 4, the snore metrics module 402 can include a distance determination module 404 and a snore data module 406.

The distance determination module 404 can determine (or estimate) a distance (or proximity) between a wrist on which a user is wearing a wearable device (e.g., the wearable device 200 of FIG. 2) and the mouth of the user. In various embodiments, the determined distance can be used to improve the accuracy of various snore metrics for the user. For example, in some embodiments, the determined distance can be used to improve the accuracy of a snore intensity determined for the user. In general, the snore intensity can be determined based on sound pressure levels (SPL) measured by the wearable device. The accuracy of sound pressure levels measured by the wearable device can be affected by the distance between the wearable device and the user's mouth from which the snoring originates. In various embodiments, to help improve their accuracy, sound pressure levels measured by the wearable device can be corrected based on the determined distance between the wrist on which the user is wearing the wearable device and the mouth of the user. For example, a snore that was determined to be very intense (e.g., 70 dB) due to the wearable device being positioned near to the user's mouth can be recategorized as being moderately intense (e.g., 50 dB) by accounting for the close distance between the wearable device and the user's mouth. In various embodiments, the distance determination module 404 can measure distances based on a specified height of the user of the wearable device. For example, an arm length of the user can be estimated based on the height of the user. For example, the arm length can be estimated as some fraction of the height. The estimated arm length can be used to correct estimated distances. In various embodiments, the distance determination module 404 can determine (or estimate) a distance between the wearable device and the mouth of the user based on poses of the user of the wearable device. For example, in various embodiments, the distance determination module 404 can determine (or estimate) a wrist pose of the user. In some embodiments, the wrist pose can be determined based on an orientation of the wearable device and attitude of the wearable device to magnetic north. For example, the orientation of the wearable device can be determined based on an angle of a face of the wearable device (e.g., display screen) and a gravity vector determined by one or more accelerometers in the wearable device. Further, the attitude of the wearable device can be determined based on one or more magnetometers in the wearable device. In some embodiments, location information accessible to the wearable device and/or a computing device in communication with the wearable device can be used to account for changes to magnetic north. For example, in some embodiments, a WiFi signal can be used to determine whether the user is at home or at another location. In such embodiments, the determined location can be used to adjust the direction of magnetic north, thereby improving the accuracy of the attitude of the wearable device. Once the wrist pose is determined, the distance determination module 404 can determine (or estimate) one or more sleep (or body) poses of the user. For example, the distance determination module 404 can determine the sleep poses by shrinking down the space of potential sleep poses based on a rigid human pose model. The rigid human pose model can shrink the space of potential sleep poses based on the determined wrist pose and human musculoskeletal limitations. In various embodiments, the distance determination module 404 can also shrink down the space of potential sleep poses based on the assumption that entities that snore typically sleep in a supine (or facing up) position. In general, sleeping in non-supine positions can make snoring more difficult, since such positions are less likely to cause relaxed tissues in the entity's throat to vibrate as the entity inhales and exhales. In various embodiments, the distance determination module 404 can implement a function that maps a set of inputs, such as wearable device orientation and attitude, to one or more potential wrist poses and sleep poses. In some embodiments, a wrist and sleep pose of the user can be determined (or estimated) based on a ballistocardiogram (BCG) pattern detected by the wearable device. For example, the BCG pattern can be determined by one or more accelerometers in the wearable device. In various embodiments, the BCG pattern can represent propagation of heartbeats from the user's heart to the user's wrist on which the wearable device is worn over some period of time. In such embodiments, certain propagation patterns can be indicative of certain poses. As a result, the BCG pattern can be correlated to the user's wrist pose and/or sleep pose. In various embodiments, the distance determination module 404 can implement a function that maps a BCG pattern to one or more potential wrist poses and/or sleep poses.

The snore data module 406 can generate various snore information for the user based on the user's snoring activity. For example, the snore data module 406 can obtain audio data recording (or capturing) the user's snoring activity over some period of time (e.g., overnight). The snore data module 406 can evaluate the obtained audio data to determine snore information for the user. For example, in some embodiments, the snore data module 406 can determine snore level measurements based on the audio data of the user's snoring activity. For example, the snore level measurements can be determined based on the user's snoring activity recorded over the period of time. In some embodiments, each snore level measurement can provide a measurement of sound that was detected and recorded by the audio data. For example, in some embodiments, a snore level measurement can be measured using decibels (dB). In various embodiments, the snore level measurements can be represented in one or more visual graphs, as illustrated in the examples of FIGS. 6A-6J. In some embodiments, the snore data module 406 can determine sound level measurements based on the audio data of the user's snoring activity recorded over the period of time. The sound level measurements can measure any sounds that were detected over the period of time including ambient (or environmental) noise. In some embodiments, the snore data module 406 can determine durations of snoring activity. For example, once the snore data module 406 determines a snore in the audio data, the snore data module 406 can determine (or estimate) a length of time during which the snore occurred. In various embodiments, durations of snoring activity can be represented in one or more visual graphs, as illustrated in the examples of FIGS. 6A-6J. In some embodiments, the snore data module 406 can determine snore intensity measurements based on the audio data of the user's snoring activity recorded over the period of time. For example, a snore intensity measurement for a snore can be determined by correcting a snore level measurement for the snore based on a distance from a microphone that recorded the snore and the user's mouth that produced the snore. In some embodiments, multiple microphones can be used to record the user's snoring activity to improve distance estimation. In various embodiments, the snore intensity measurements can be represented in one or more visual graphs, as illustrated in the examples of FIGS. 6A-6J.

In some embodiments, the snore data module 406 can determine various types of sound events based on the audio data of the user's snoring activity. For example, a sound event can correspond to ambient noise or a sound produced by the user. Further, a sound event may refer to a snore, a sleep apnea event, movement noise, heavy breathing, or ambient noise, to name some examples. In various embodiments, the sound events can be represented in one or more visual graphs, as illustrated in the examples of FIGS. 6A-6J. In some embodiments, such visual graphs can provide an option (or visual indicator) for replaying sound events that were detected when the user's was sleeping. In such embodiments, the option can be selected to replay the sound event. In some embodiments, the snore data module 406 can identify sound events that occurred just before a change was detected in the user's sleep state. For example, if the user abruptly transitions from a deep sleep state to an awake state, the snore data module 406 can determine and extract any sound events that occurred just before the change in the user's sleep state. In this example, the snore data module 406 can provide an option to replay the sound event so that the user can more easily identify sources of sound that are disturbing the user during sleep. Many variations are possible.

Figure 5:
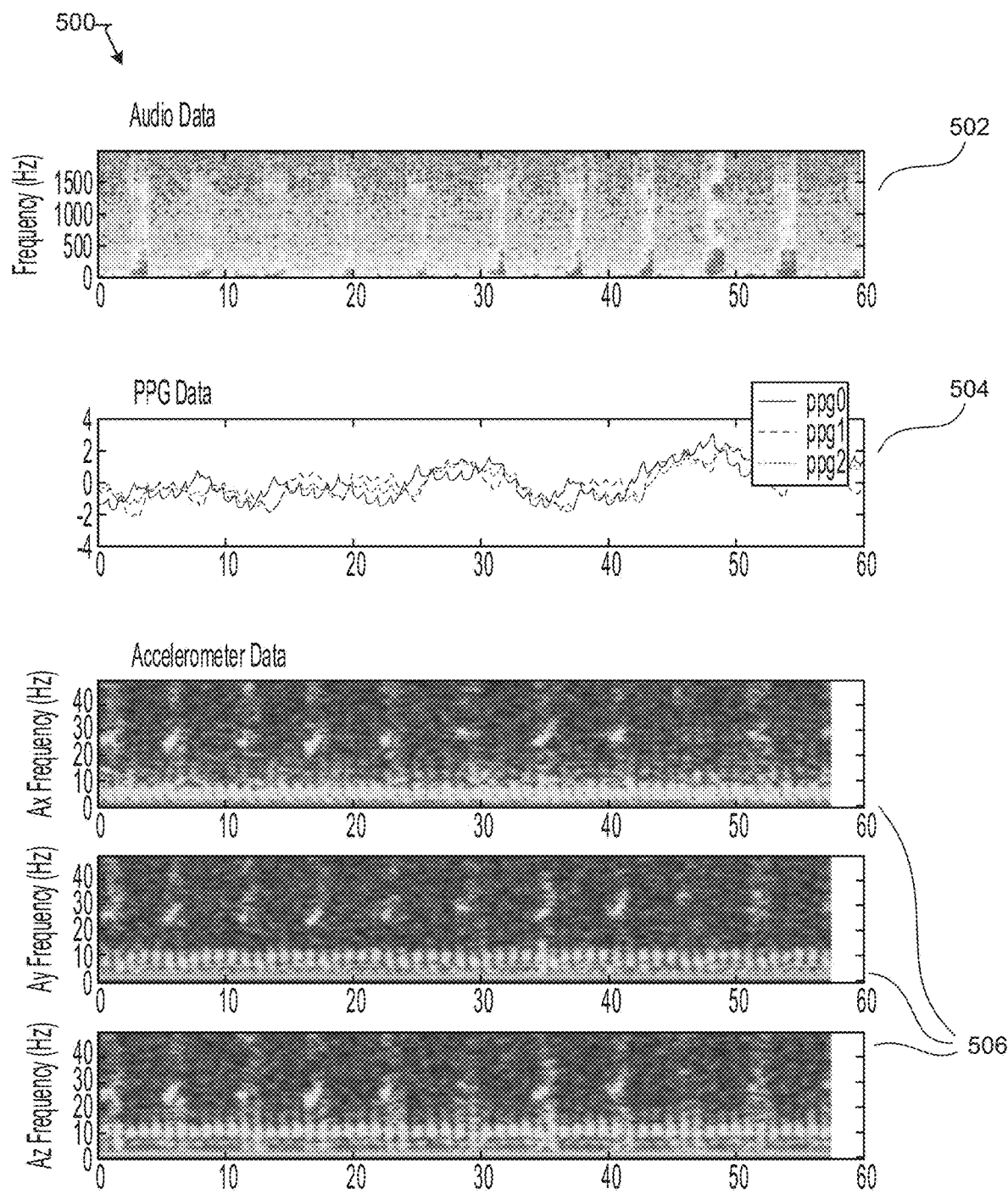
FIG. 5 illustrates an example diagram of captured audio and sensor data, according to an embodiment of the present technology.

FIG. 5 illustrates an example diagram 500 of audio and sensor data captured over some period of time. For example, the diagram 500 illustrates audio data 502 captured by a microphone, photoplethysmogram (PPG) sensor data 504 captured by PPG sensors (e.g., green PPG sensor, red PPG sensor, and infrared PPG sensor), and sensor data 506 captured by an accelerometer over some period of time. In the example diagram 500, the audio data 502 represents spectral properties of audio that was detected and recorded as a user of a wearable device (e.g., the wearable device 200 of FIG. 2) was sleeping. Similarly, the PPG sensor data 504 captured by the PPG sensors represents physiological measurements that were recorded by the wearable device while the user was sleeping. Further, the sensor data 506 captured by the accelerometer represents motion or vibration detected by the wearable device while the user was sleeping. The diagram 500 helps visualize correlations between the audio and sensor data that can be used to determine various information for the user, as described herein. For example, the audio data 502, the PPG data 504, and the accelerometer data 506 can each be used independently to determine a breathing (or respiratory) rate for the user. In another example, the correlations between the audio data 502 and sensor data (e.g., PPG data 504, accelerometer data 506) can be used to determine whether the user of the wearable device is snoring, as described above. Many variations are possible.

Figure 6A:
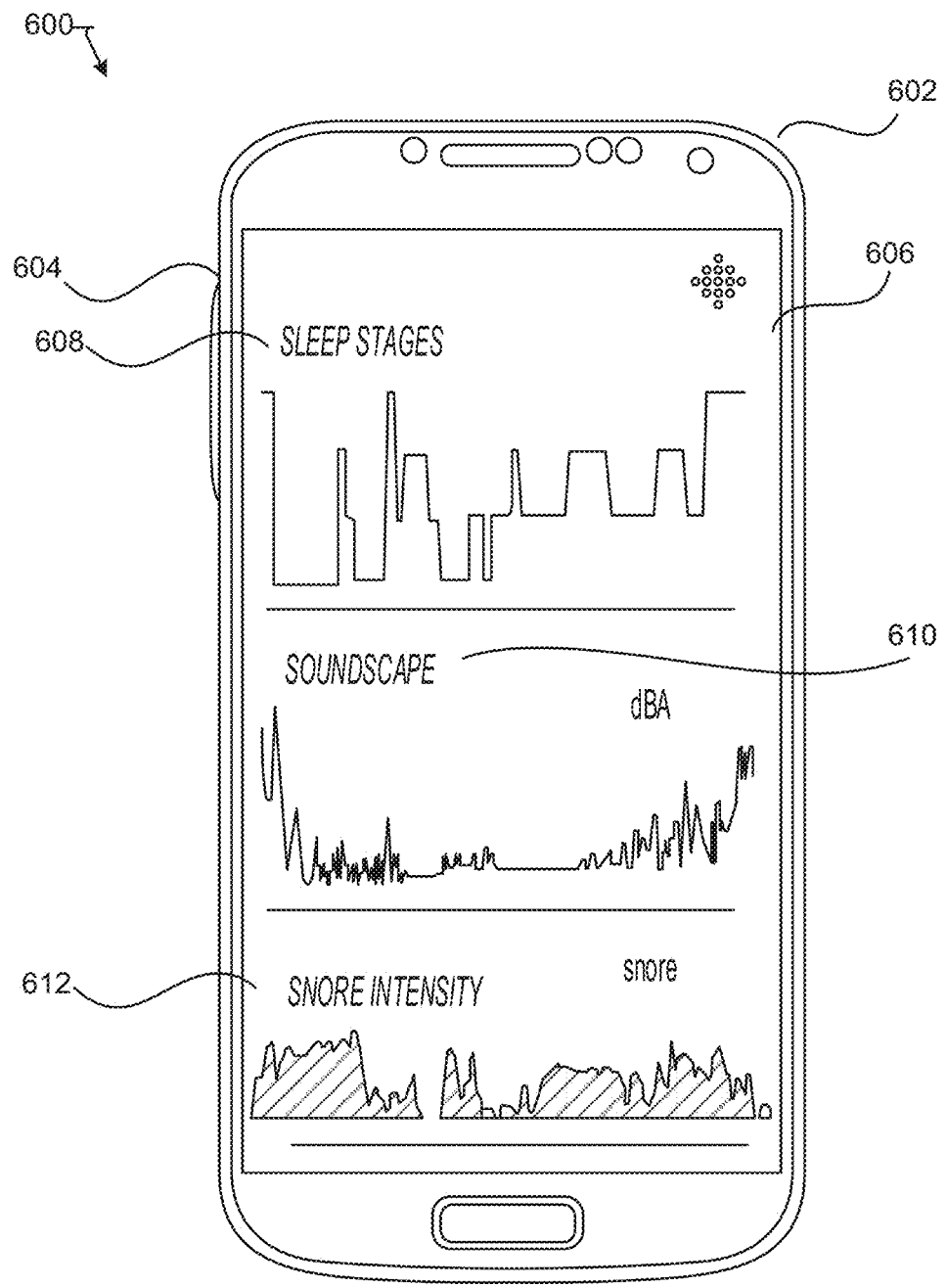
Figure 6B:
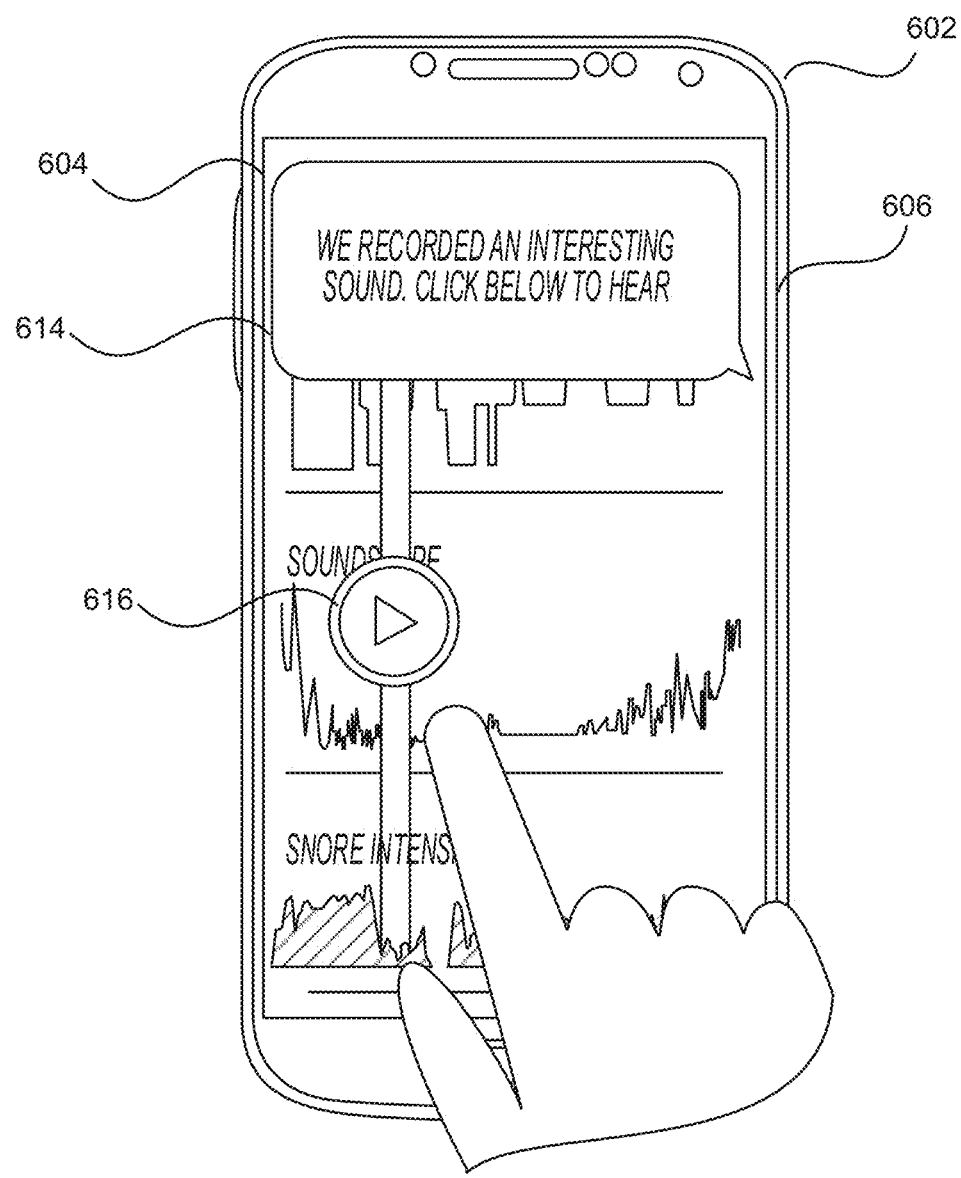
Figure 6C:
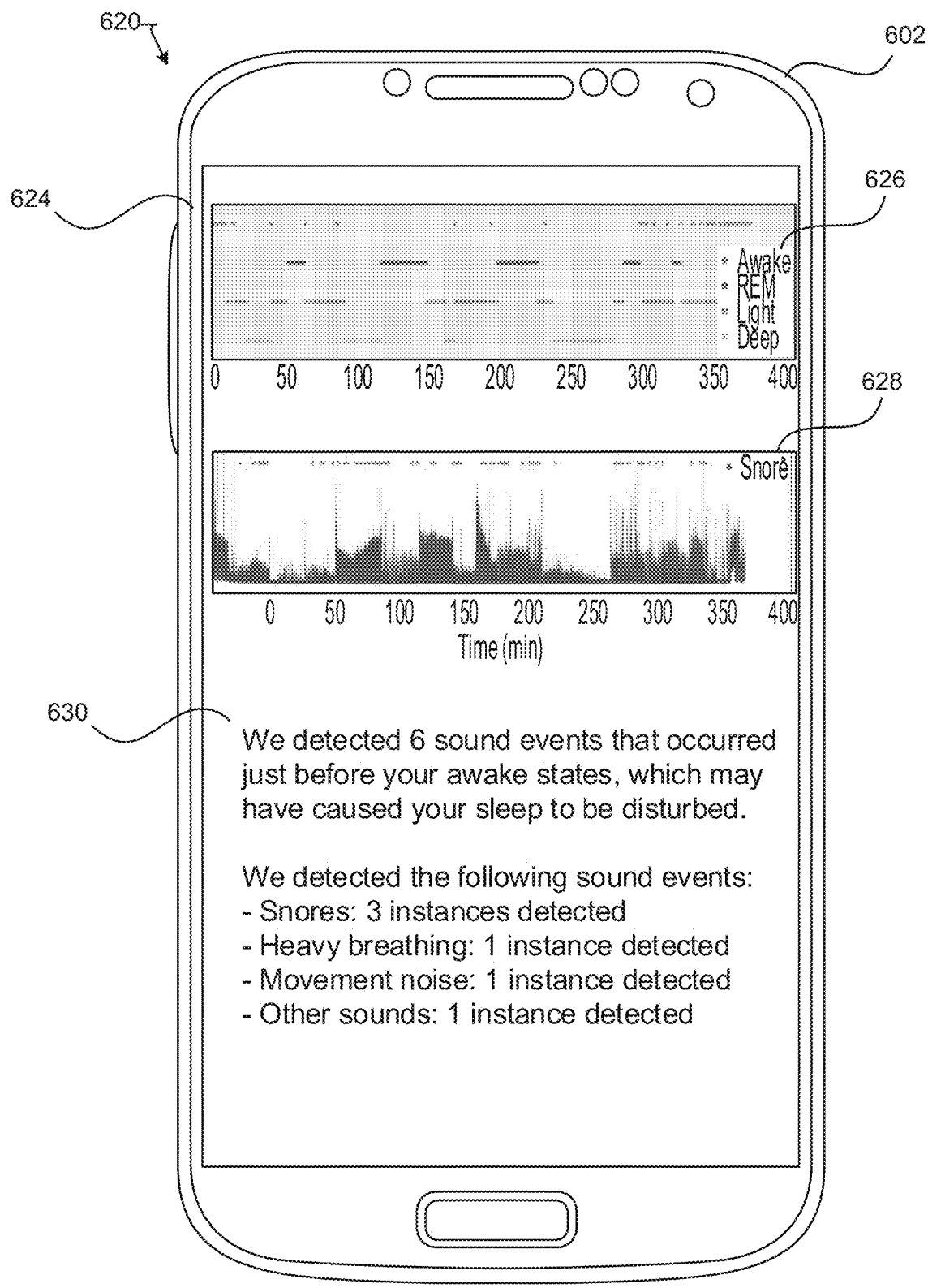
Figure 6D:
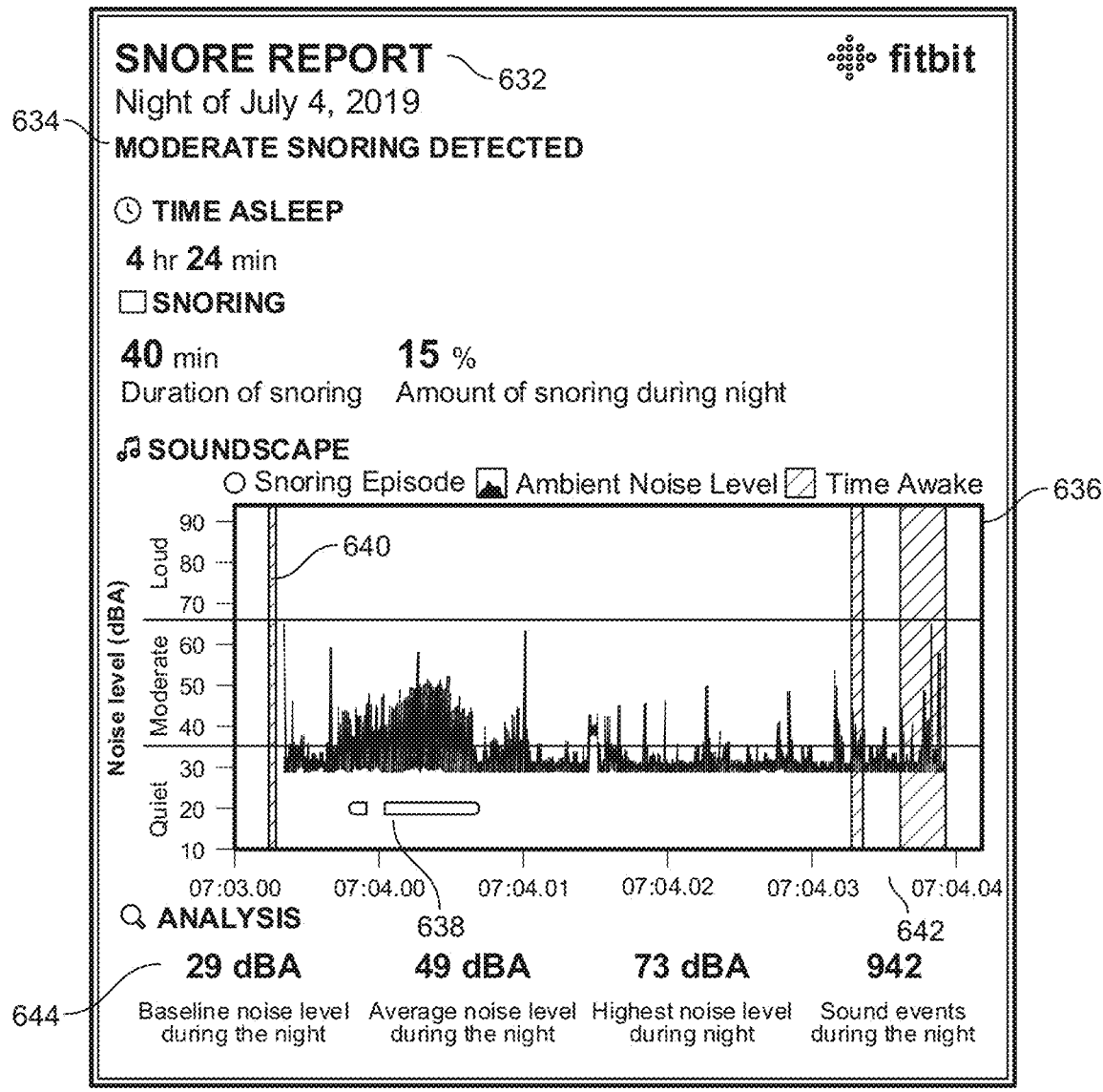

FIG. 6A illustrates an example 600 of an interface 604, according to an embodiment of the present disclosure. The interface 604 is presented on a display screen of a computing device, such as the computing device 602 or a wearable device (e.g., the wearable device 200 of FIG. 2). The interface 604 may be provided through an application (e.g., a web browser, a fitness application, etc.) running on the computing device 602. In this example, the interface 604 is providing a snore graph 606 that plots various information determined for a user of the wearable device. For example, the snore graph 606 includes a first visual graph 608 representing the user's sleep states as detected by the wearable device. For example, the first visual graph can visually represent changes to the user's sleep state when the user was sleeping over some period of time. In some embodiments, the user's sleep states may be categorized as one of an awake state, a rapid eye movement (REM) state, a light sleep state, and a deep sleep state. Many variations are possible. The snore graph 606 also includes a second visual graph 610 that represents sound level measurements determined as the user slept over the period of time. For example, each sound level measurement can represent an amount of sound that was detected at some point of time from audio data recording the user's sleep activity. Further, the snore graph 606 also includes a third visual graph 612 that represents snore intensity measurements determined as the user slept over the period of time. The snore graph 606 provides a detailed assessment of the user's sleep activity while allowing for comparison between the user's sleep state, sound level measurement, and snore intensity at any given point in time during the user's sleep activity. In various embodiments, the snore graph 606 can provide options for replaying sound events that were detected during the user's sleep activity. For example, the interface 604 in FIG. 6B shows a message 614 indicating an interesting sound event was detected during the user's sleep activity. The interface 604 also provides an option (or a visual indicator) 616 that can be selected to replay a recording of the interesting sound event. Many variations are possible.

FIG. 6C illustrates an example 620 of an interface 624, according to an embodiment of the present disclosure. The interface 624 is presented on a display screen of the computing device 602 or the wearable device. The interface 624 may be provided through an application (e.g., a web browser, a fitness application, etc.) running on the computing device 602. The interface 624 can provide various information determined for a user of the wearable device. In this example, the interface 624 provides a first visual graph 626 that plots changes to a user's sleep state over some period of time. In some embodiments, the user's sleep states may be categorized as one of an awake state, a rapid eye movement (REM) state, a light sleep state, and a deep sleep state. The interface 624 also includes a second visual graph 628 that plots sound levels (e.g., decibel levels) that were measured over the period of time while the user was sleeping. In various embodiments, the interface 624 can provide information 630 describing the types of sound events that were detected while the user was sleeping. In some embodiments, the information 630 can provide a total count of sound events that may have contributed to the user going from a sleep state (e.g., REM, light sleep, deep sleep) to an awake state as well as respective counts of specific types of sound events (e.g., snores, heavy breathing, movement noise, etc.) that may have woken the user. In some embodiments, the information 630 can provide a total count of sound events that were detected during the entirety of the user's sleep activity as well as respective counts of specific types of sound events (e.g., snores, heavy breathing, movement noise, etc.). In some embodiments, the information 630 can provide tips (or insights) for improving sleep habits. For example, the information 630 can inform the user that the user woke up several times last night after noisy sound events were detected. In another example, the information 630 can inform the user that another entity's snoring (e.g., the user's partner) may be affecting the user's sleep. In yet another example, the information 630 can provide the user with access to one or more audio recordings of sound events, such as snores and apnea events, that can be shared with the user's medical professional for further analysis. In yet another example, the information 630 can inform the user of an overall sound level associated with their sleep environment as compared to other sleep environments (e.g., "Your sleep environment is quieter than 90 percent of other users"). Many variations are possible.

FIG. 6D illustrates an example snore report 632 that can be provided for presentation through an interface of a computing device, such as the computing device 602 or a wearable device (e.g., the wearable device 200 of FIG. 2). The interface may be provided through an application (e.g., a web browser, a fitness application, etc.) running on the computing device 602. The snore report 632 can provide various information determined for a user of the wearable device. The snore report 632 can provide a summary of the user's sleep activity for a given day. For example, the snore report 632 can provide a total amount of time a user was determined to be asleep for the day. The snore report 632 can also describe the user's snoring activity for the day, including a total duration of the snoring activity (e.g., "40 min") and/or a percentage representing the user's snoring activity relative to the amount of time the user was determined to be asleep (e.g., "15%"). In some embodiments, the snore report 632 can categorize and provide the user's snoring activity based on snoring intensity 634 (e.g., "moderate snoring detected"). For example, the snoring activity can be categorized as "quiet", "moderate", or "loud" based on snoring intensity. In some embodiments, the snore report 632 can provide a visual graph 636 that plots the user's sleep activity for the day. For example, the visual graph 636 can identify portions 638 of the sleep activity that correspond to a snoring episode. The visual graph 636 can also identify portions 640 of the sleep activity during which ambient noise was detected and can also indicate a corresponding noise level (e.g., dBA). Further, the visual graph 636 can identify portions 642 of the sleep activity during which the user was determined to be awake. In some embodiments, the snore report 632 can provide a noise-level analysis 644 that can indicate one or more of: a baseline noise level during the user's sleep activity, an average noise level during the user's sleep activity, a highest noise level during the user's sleep activity, and a count of sound events detected during the user's sleep activity. Many variations are possible.

Figure 6E:
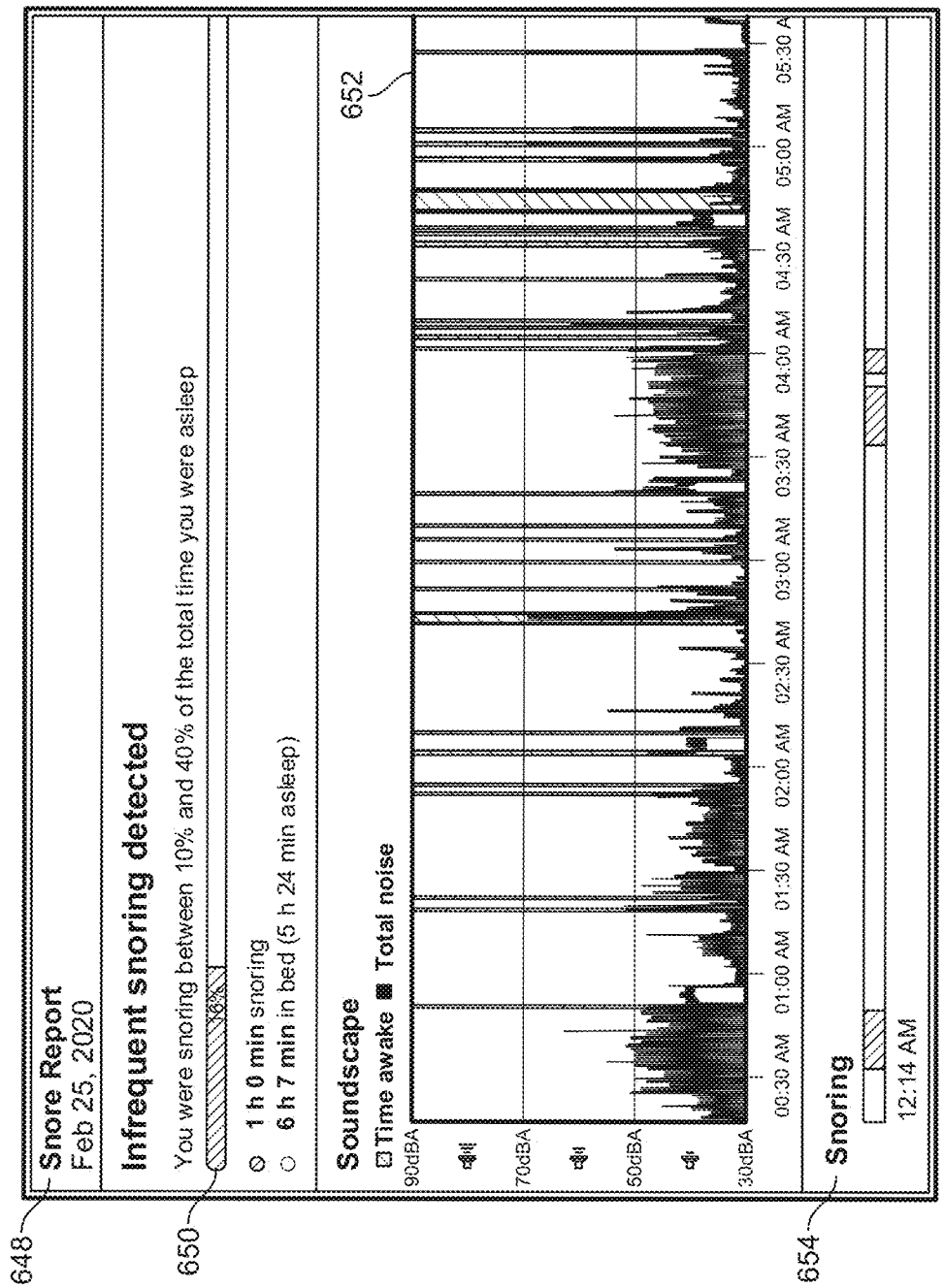

FIG. 6E illustrates another example snore report 648 that can be provided for presentation through an interface of a computing device, such as the computing device 602 or a wearable device (e.g., the wearable device 200 of FIG. 2). The snore report 648 can provide various information determined for a user of the wearable device. In various embodiments, the snore report 648 can provide a summary of the user's sleep activity for a given day as determined using any of the approaches described herein. For example, the snore report 648 can provide a total amount of time a total amount of time the user was determined to be in bed (e.g., "6 h 7 min in bed"), a total amount of time the user was determined to be asleep (e.g., "5 h 24 min asleep"), and a total amount of time the user was determined to be snoring (e.g., "1 h 0 min snoring"). In some embodiments, the snore report 648 can categorize and provide the user's snoring activity based on snoring intensity 650 (e.g., "Infrequent snoring detected"). In some embodiments, the snore report 648 can indicate a percentage range representing the user's snoring activity relative to the amount of time the user was determined to be asleep (e.g., "You were snoring between 10% and 40% of the total time you were asleep"). In some embodiments, the snore report 648 can provide a visual graph 652 that plots the user's sleep activity. For example, the visual graph 652 can identify portions of the sleep activity during which ambient noise was detected and can also indicate a corresponding noise level (e.g., dBA). Further, the visual graph 652 can identify portions of the sleep activity during which the user was determined to be awake. In some embodiments, the snore report 648 can indicate portions 654 of the sleep activity during which the user was determined to be asleep. Many variations are possible.

Figure 6F:
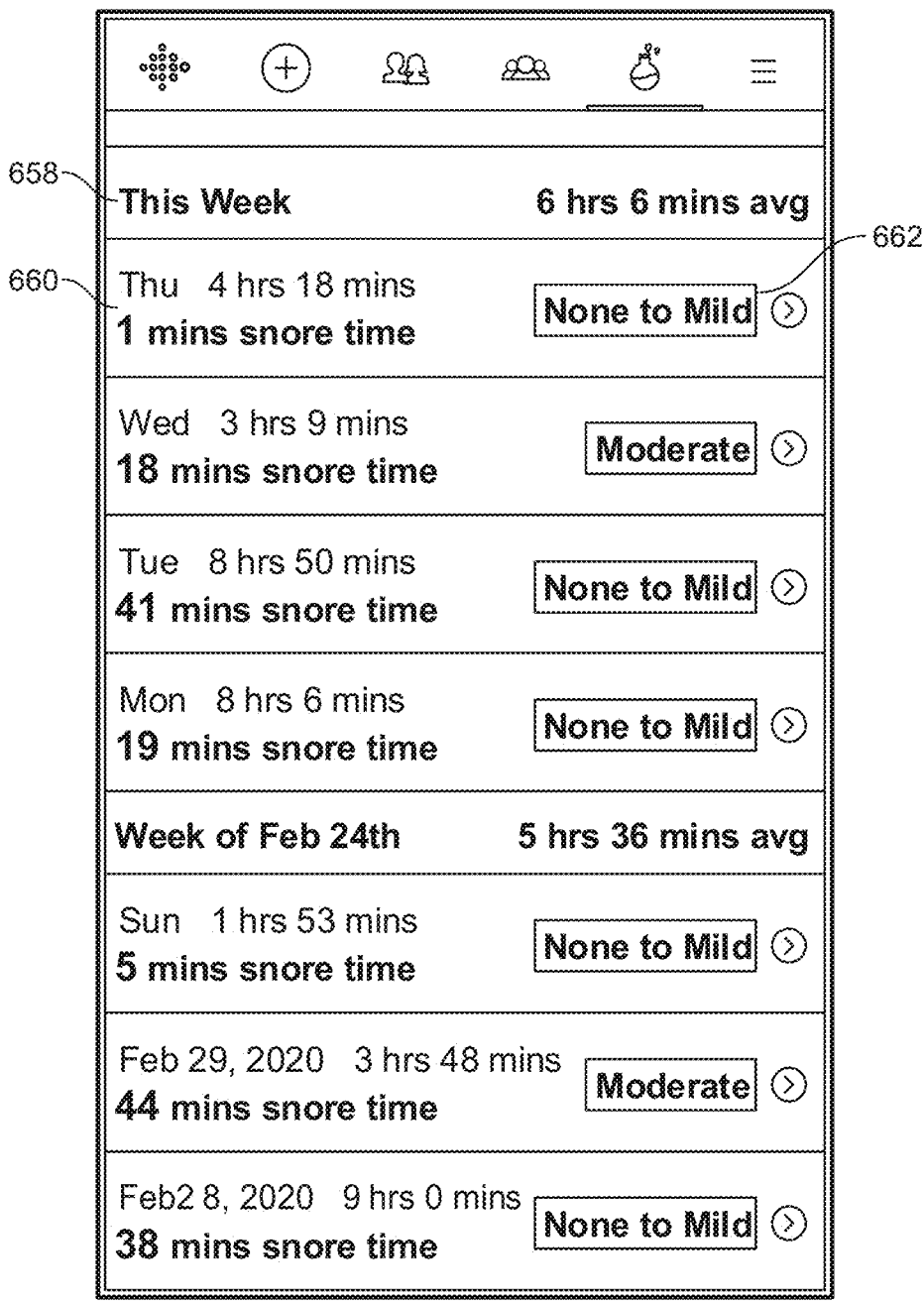

FIG. 6F illustrates another example snore report 658 that can be provided for presentation through an interface of a computing device, such as the computing device 602 or a wearable device (e.g., the wearable device 200 of FIG. 2). The snore report 658 can provide various information determined for a user of the wearable device. In various embodiments, the snore report 658 can provide a sleep summary for various periods of time (e.g., weekly, monthly, etc.). For example, the snore report 658 can provide an average amount of sleep for the user over the period of time (e.g., "6 hrs 6 min avg"). Further, for a given day 660, the snore report 658 can indicate a total amount of time a user was determined to be asleep and a total amount of time the user was determined to be snoring. In some embodiments, the snore report 658 can provide a snore level (or categorization) 662 for the day. The snore level 662 can be determined based on a classification of the user's snoring intensity for the day. For example, depending on the snoring intensity, the snore level 662 can be classified as "None to Mild", "Moderate", or "Loud". Naturally, many variations are possible.

FIG. 6G illustrates sound level information 664 that may be provided for presentation through an interface of a computing device, such as the computing device 602 or a wearable device (e.g., the wearable device 200 of FIG. 2). The sound level information 664 can provide various information determined for a user of the wearable device. For example, in some embodiments, the sound level information 664 can be provided in a snore report. The sound level information 664 can indicate a typical sound level in the user's sleep location (e.g., bedroom). The sound level can be determined based on an amount of snoring and background noise detected at the user's sleep location while the user was determined to be asleep, for example.

Figure 6K:
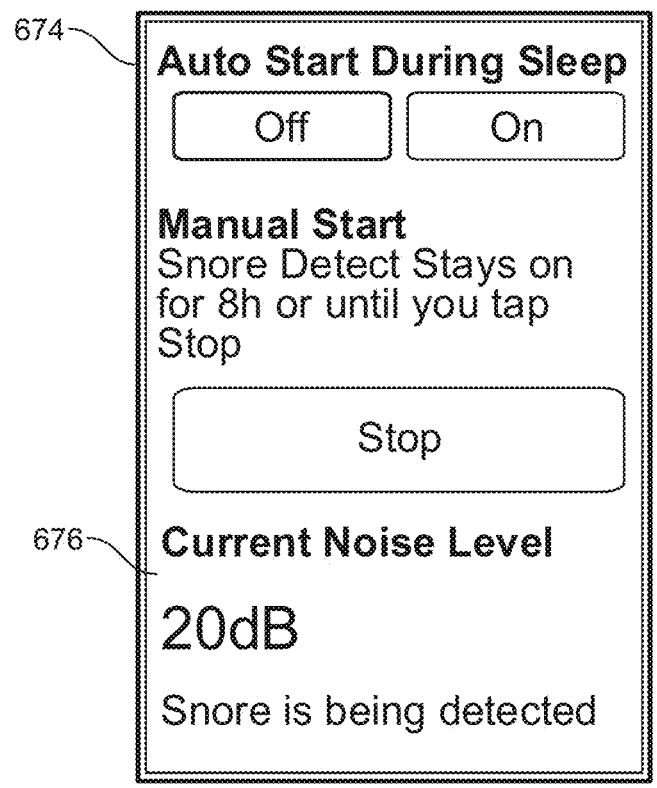

FIGS. 6H-6J illustrates various types of error information that can be provided for presentation through an interface of a computing device, such as the computing device 602 or a wearable device (e.g., the wearable device 200 of FIG. 2). For example, in some embodiments, the error information can be provided in a snore report to assist a user of the wearable device troubleshoot sleep detection and/or snore detection issues. For example, FIG. 6H illustrates an error message 668 indicating the user's snoring was not able to be recorded due to an inconsistent sleep pattern. The error message 668 can also provide instructions to address the error. In this example, the error message 668 can ask the user to enable a manual recording mode before sleeping to facilitate the recording of the user's snoring, as illustrated in the example of FIG. 6K. In another example, FIG. 6I illustrates an error message 670 which indicates that snoring recorded for the user may be inconclusive because the wearable device ran out of battery. The error message 670 can ask the user to charge the wearable device to a certain battery level before sleeping. In yet another example, FIG. 6J illustrates an error message 672 which indicates the user's snoring could not be recorded due to excessive background noise. The user can then take actions to reduce background noise to facilitate a more complete recording of the user's snoring. Many variations are possible.

FIG. 6K illustrates an interface 674 with options for configuring a wearable device (e.g., the wearable device 200 of FIG. 2). The interface 674 may be accessible through a computing device, such as the computing device 602 or the wearable device. As shown, the interface 674 can provide options to enable automatic snore detection or manual snore detection. The interface 674 can also provide an option to disable snore detection entirely. Further, the interface 674 can indicate a current noise level 676 detected by the wearable device. Many variations are possible.

Figure 7:
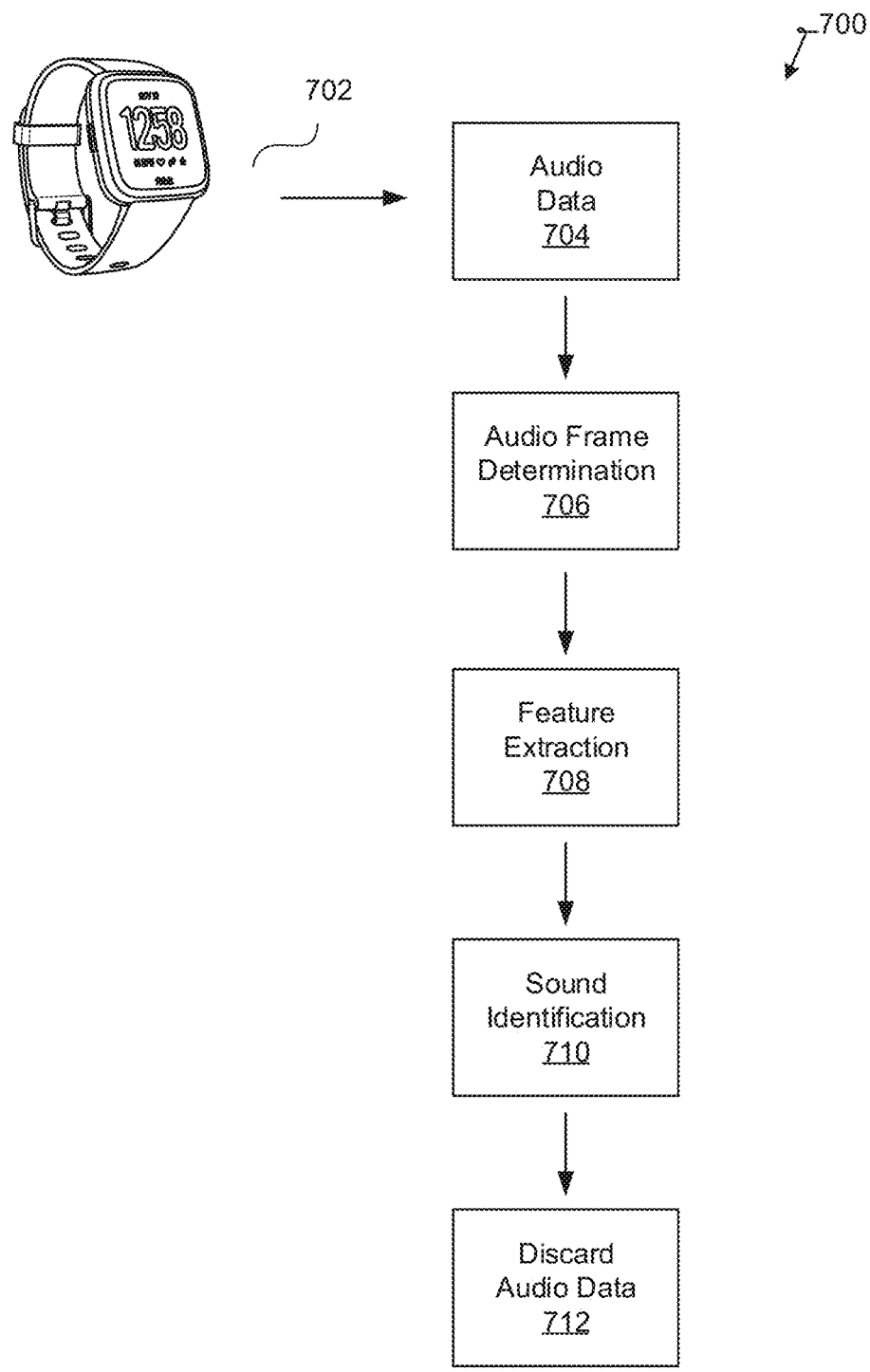

FIG. 7 illustrates an example method 700, according to an embodiment of the present technology. Naturally, the method 700 may include additional, fewer, or alternative steps and these steps may be performed individually or in parallel within the scope of the various embodiments discussed herein unless otherwise stated.

At block 704, audio data can be captured over some period of time. The audio data can capture sounds that occurred while a user of a wearable device 702 was determined to be sleeping. Depending on the embodiment, the audio data may be captured by one or more microphones in the wearable device 702 (e.g., the wearable device 200 of FIG. 2), by one or more standalone microphones that are separate from the wearable device 702, or a combination thereof. At block 706, the captured audio data can be segmented into one or more audio frames that each represent some portion of the captured audio data. At block 708, respective sets of features can be extracted from each audio frame. For example, a set of features extracted from an audio frame can include mel-frequency cepstral coefficients (MFCCs) that describe a spectrum of frequencies represented by the audio frame. At block 710, the sets of features can be categorized as one or more sounds that were detected in the captured audio data, as described herein. At block 712, the captured audio data can be discarded (or deleted) after the one or more sounds are categorized. In some embodiments, each audio frame can be deleted on-the-fly as soon as the audio frame has been analyzed and categorized. Many variations are possible.

FIG. 8A illustrates an example method 800, according to an embodiment of the present technology. Naturally, the method 800 may include additional, fewer, or alternative steps and these steps may be performed individually or in parallel within the scope of the various embodiments discussed herein unless otherwise stated.

At block 802, one or more breathing phase patterns can be determined over a period of time using audio data captured by at least one microphone, the audio data including one or more snores. At block 804, a breathing phase pattern included within the period of time can be determined, based at least in part on sensor data captured by one or more sensors in an electronic device. At block 806, a determination is made that a first breathing phase pattern represented by the audio data, and a second breathing phase pattern represented by the sensor data are correlated. At block 808, a determination is made that the first breathing phase pattern represented by the audio data and the second breathing phase pattern represented by the sensor data both correspond to a user wearing the electronic device.

FIG. 8B illustrates an example method 850, according to an embodiment of the present technology. Naturally, the method 850 may include additional, fewer, or alternative steps and these steps may be performed individually or in parallel within the scope of the various embodiments discussed herein unless otherwise stated.

At block 852, an audio signal can be captured using at least one microphone while a user of an electronic device is determined to be asleep. At block 854, at least one audio frame can be determined from the audio signal. The audio frame can represent a spectrum of frequencies detected by the at least one microphone over some period of time. At block 856, one or more sounds associated with the at least one audio frame can be determined. At block 858, sleep-related information can be generated. The sleep-related information can identify the one or more sounds as potential sources of sleep disruption.

Figure 9:
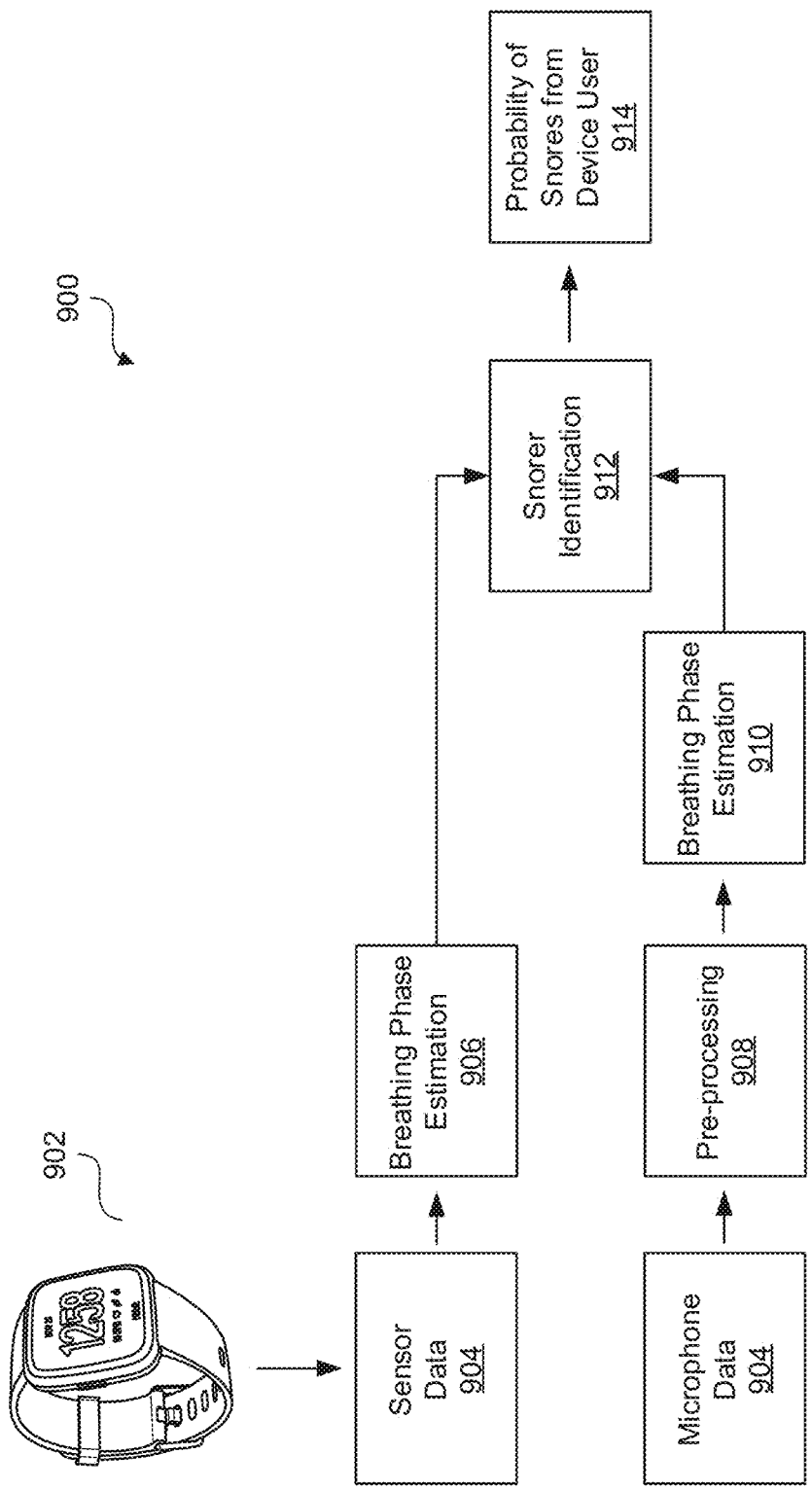

FIG. 9 illustrates an example method 900, according to an embodiment of the present technology. Naturally, the method 900 may include additional, fewer, or alternative steps and these steps may be performed individually or in parallel within the scope of the various embodiments discussed herein unless otherwise stated.

At block 904, one or more sensors in a wearable device 902 (e.g., the wearable device 200 of FIG. 2) can capture sensor data over some period of time. For example, the sensor data can be data captured by one or more photoplethysmogram (PPG) sensors in the wearable device 902. In another example, the sensor data can be data captured by one or more accelerometers in the wearable device 902. Also at block 904, audio data can be captured by one or more microphones over the same period of time over which the sensor data is captured. The audio data can capture an entity that is snoring. Depending on the embodiment, the audio data may be captured by one or more microphones in the wearable device 902, by one or more standalone microphones that are separate from the wearable device 902, or a combination thereof. At block 906, a breathing phase can be determined (or estimated) based on the sensor data captured by the one or more sensors in the wearable device 902. At block 908, the audio data captured by the one or more microphones can optionally be pre-processed, as described above. At block 910, a breathing phase can be determined (or estimated) based on the audio data captured by the one or more microphones. At block 912, a determination is made whether the breathing phase represented by the sensor data corresponds (or correlates) to the breathing phase represented by the audio data, as described above. If a correspondence exists, a determination can be made that the snoring captured in the audio data originates from a user of the wearable device 902. At block 914, a probability that measures a likelihood of the snoring captured by the audio data being associated with the user of the wearable device 902. Many variations are possible.

Figure 10:
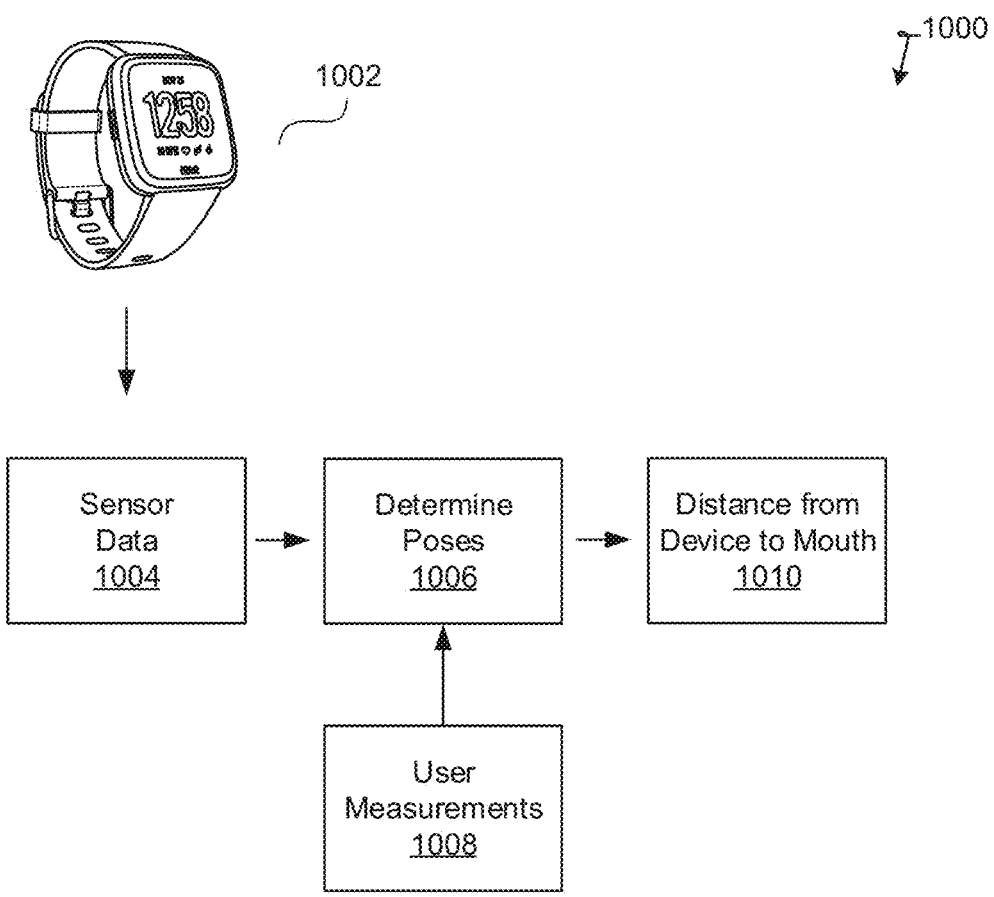

FIG. 10 illustrates an example method 1000, according to an embodiment of the present technology. Naturally, the method 1000 may include additional, fewer, or alternative steps and these steps may be performed individually or in parallel within the scope of the various embodiments discussed herein unless otherwise stated.

At block 1004, one or more sensors in a wearable device 1002 (e.g., the wearable device 200 of FIG. 2) can capture sensor data over some period of time. For example, the sensor data can be data captured by one or more accelerometers and magnetometers in the wearable device 1002. At block 1006, one or more wrist and sleep poses can be determined for a user of the wearable device 1002. For example, the wrist and sleep poses can be determined based on the captured sensor data, as described above in reference to FIG. 4. At block 1008, measurements (e.g., height) of the user can be used to refine the wrist and sleep poses of the user. At block 1010, a distance between the wearable device 1002 and the mouth of the user can be determined (or estimated) based on the wrist and sleep poses of the user, as described above in reference to FIG. 4. Many variations are possible.

Figure 11:
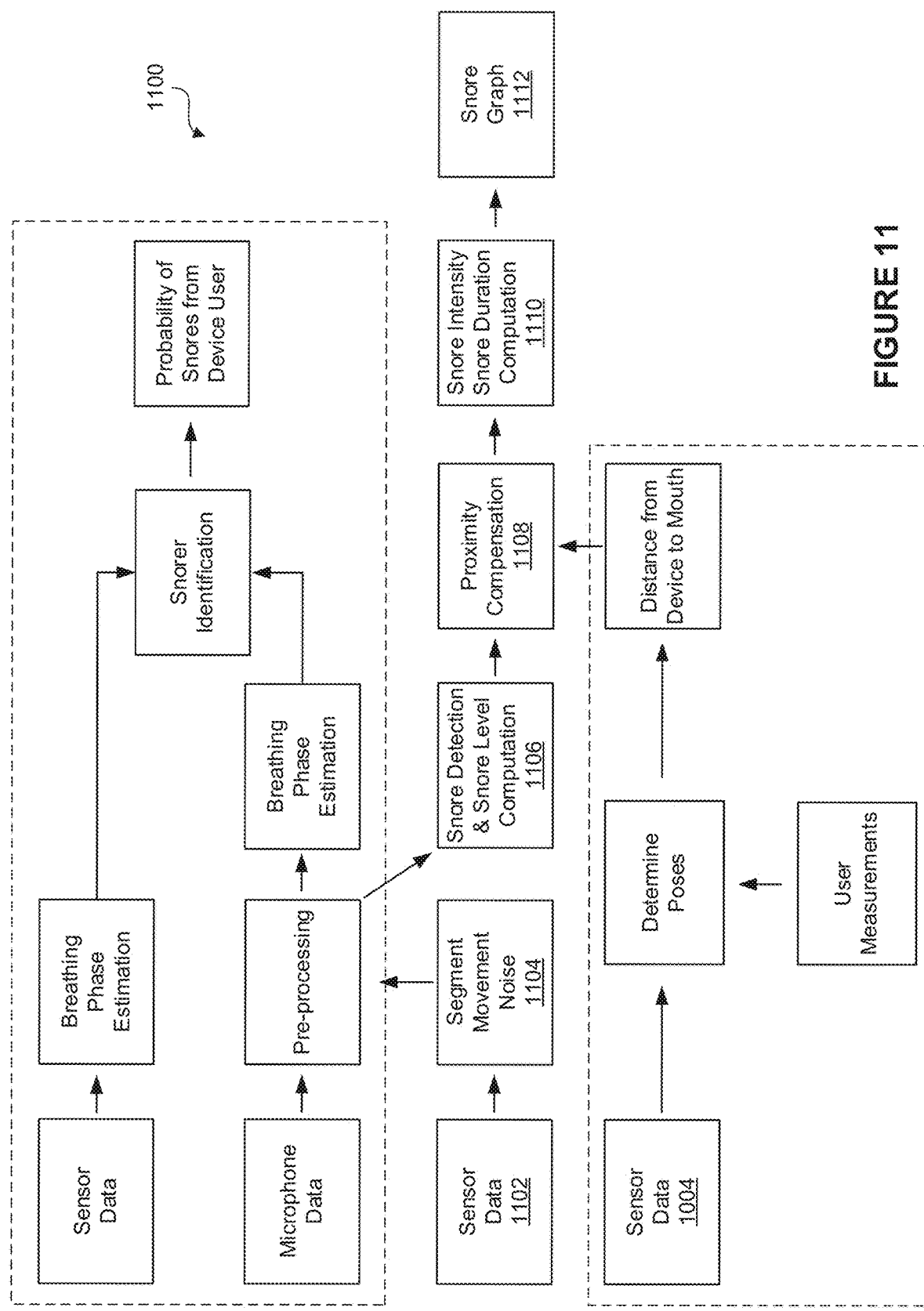

FIG. 11 illustrates an example method 1100, according to an embodiment of the present technology. Naturally, the method 1100 may include additional, fewer, or alternative steps and these steps may be performed individually or in parallel within the scope of the various embodiments discussed herein unless otherwise stated.

At block 1102, one or more sensors in a wearable device (e.g., the wearable device 200 of FIG. 2) can capture audio and sensor data over some period of time. For example, the audio data can be recorded (or captured) by one or more microphones in the wearable device. The audio data can record sounds that were detected as a user of the wearable device was sleeping. The sensor data can be data captured by one or more accelerometers and magnetometers in the wearable device, for example. At block 1104, movement noise recorded in the audio data can be segmented (or dropped) from the audio data to improve snore detection accuracy. In some embodiments, the movement noise can be identified by correlating motion detected by sensors in the wearable device, such as one or more accelerometers and photoplethysmogram (PPG) sensors. In some embodiments, the movement noise can be segmented by pre-processing the audio data, as described above in reference to FIG. 9. At block 1106, the audio and sensor data can be used to detect snores produced by the user during sleep as well as snore level measurements, as described above. At block 1108, the snore level measurements can be corrected based on a distance between the user's mouth and a microphone recording snores originating from the user's mouth, as described in reference to FIG. 10. At block 1110, snore intensity and duration measurements can be determined for the user, as described above. At block 1112, a snore graph visualizing changes to the user's sleep state, sound level measurements, and snore intensity over some period of time can be generated, as illustrated in the example of FIG. 6A. Many variations are possible.

Naturally, there may be many other users, applications, and/or variations of the various embodiments described herein. For example, in some cases, user can choose whether or not to opt-in to utilize the disclosed technology. The disclosed technology can also ensure that various privacy settings and preferences are maintained and can prevent private information from being divulged.

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Although an overview of the subject matter has been described with reference to specific example embodiments, various modifications and changes may be made to these embodiments without departing from the broader scope of embodiments of the present disclosure. Such embodiments of the subject matter may be referred to herein, individually or collectively, by the term "invention" merely for convenience and without intending to voluntarily limit the scope of this application to any single disclosure or concept if more than one is, in fact, disclosed.

The embodiments illustrated herein are described in sufficient detail to enable those skilled in the art to practice the teachings disclosed. Other embodiments may be used and derived therefrom, such that structural and logical substitutions and changes may be made without departing from the scope of this disclosure. The Detailed Description, therefore, is not to be taken in a limiting sense, and the scope of various embodiments is defined only by the appended claims, along with the full range of equivalents to which such claims are entitled.

It will be appreciated that a "module," "system," "data store," and/or "database" may comprise software, hardware, firmware, and/or circuitry. In one example, one or more software programs comprising instructions capable of being executable by a processor may perform one or more of the functions of the modules, data stores, databases, or systems described herein. In another example, circuitry may perform the same or similar functions. Alternative embodiments may comprise more, less, or functionally equivalent modules, systems, data stores, or databases, and still be within the scope of present embodiments. For example, the functionality of the various systems, modules, data stores, and/or databases may be combined or divided differently.

As used herein, the term "or" may be construed in either an inclusive or exclusive sense. Moreover, plural instances may be provided for resources, operations, or structures described herein as a single instance. Additionally, boundaries between various resources, operations, modules, and data stores are somewhat arbitrary, and particular operations are illustrated in a context of specific illustrative configurations. Other allocations of functionality are envisioned and may fall within a scope of various embodiments of the present disclosure. In general, structures and functionality presented as separate resources in the example configurations may be implemented as a combined structure or resource. Similarly, structures and functionality presented as a single resource may be implemented as separate resources. These and other variations, modifications, additions, and improvements fall within a scope of embodiments of the present disclosure as represented by the appended claims. The specification and drawings are, accordingly, to be regarded in an illustrative rather than a restrictive sense.

Conditional language, such as, among others, "can," "could," "might," or "may," unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment.

Although the invention has been described in detail for the purpose of illustration based on what is currently considered to be the most practical and preferred implementations, it is to be understood that such detail is solely for that purpose and that the invention is not limited to the disclosed implementations, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. An electronic device comprising:
   at least one processor; and
   a memory storing instructions that, when executed by the at least one processor, cause the electronic device to perform:
      activating and deactivating at least one microphone according to a breathing phase pattern determined for a user that is determined to be asleep;
      capturing an audio signal while the at least one microphone is activated;
      determining an audio frame of the audio signal includes one or more sounds indicative of snoring;
      in response to determining the audio frame includes the one or more sounds indicative of snoring, discarding the audio frame; and
      generating sleep-related information, wherein the information identifies the one or more sounds as an instance of snoring.

2. The electronic device of claim 1, wherein determining the audio frame of the audio signals includes one or more sounds indicative of snoring occurs while the audio signal is being captured.

3. The electronic device of claim 1, wherein the at least one microphone used to capture the audio signal is included in one or both of the electronic device or a computing device separate from the electronic device.

4. The electronic device of claim 1, wherein the instructions further cause the electronic device to perform:
   providing the generated sleep-related information through an interface accessible through the electronic device or a computing device separate from the electronic device.

5. The electronic device of claim 4, wherein the sleep-related information provides one or more of: a total amount of time the user was determined to be sleeping, one or more periods of time during which the user was determined to be awake, or one or more periods of time during which the user was determined to be snoring.

6. The electronic device of claim 5, wherein the sleep-related information provides one or more of: a total amount of time during which the user was snoring, a percentage of time during which the user was snoring relative to the total amount of time the user was determined to be sleeping, or a percentage range of time during which the user was snoring relative to the total amount of time the user was determined to be sleeping.

7. The electronic device of claim 5, wherein the sleep-related information provides a categorization of the one or more periods of time during which the user was determined to be snoring based on snoring intensity.

8. The electronic device of claim 7, wherein the categorization labels the one or more periods of time during which the user was determined to be snoring as a first level of snoring, a second level of snoring, or a third level of snoring.

9. The electronic device of claim 5, wherein the sleep-related information identifies a correlation between one or more periods of time during which the user was determined to be awake and the one or more sounds identified as potential sources of sleep disruption.

10. The electronic device of claim 5, wherein the sleep-related information provides one or more of: a baseline noise level while the user was asleep, an average noise level while the user was asleep, a highest noise level while the user was asleep, or a total count of sounds detected while the user was asleep.

11. The electronic device of claim 1, wherein activating and deactivating the at least one microphone based on a breathing phase pattern determined for a user determined to be asleep comprises:
- activating the at least one microphone when the user inhales according to the breathing phase pattern; and
- deactivating the at least one microphone when the user exhales according to the breathing phase pattern.

12. A method, comprising:
- capturing, via one or more microphones, an audio signal while a user is asleep;
- determining, via one or more processors, an audio frame of the audio signal includes one or more sounds that are potentially disruptive to sleep;
- in response to determining the audio frame includes one or more sounds that are potentially disruptive to sleep, discarding, via the one or more processors, the audio frame; and
- generating, via the one or more processors, sleep-related information for the user, the sleep-related information identifying one or more sources of the one or more sounds.

* * * * *